US010287584B2

(12) United States Patent
Guo et al.

(10) Patent No.: US 10,287,584 B2
(45) Date of Patent: May 14, 2019

(54) COMPOUNDS AND METHODS FOR THE MODULATION OF COMP

(71) Applicants: Ionis Pharmaceuticals, Inc., Carlsbad, CA (US); Board of Regents of the University of Texas System, Austin, TX (US)

(72) Inventors: Shuling Guo, Carlsbad, CA (US); Punit P. Seth, Carlsbad, CA (US); Jacqueline T. Hecht, Houston, TX (US); Karen LaShea Posey, Houston, TX (US)

(73) Assignees: IONIS PHARMACEUTICALS, INC., Carlsbad, CA (US); THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/526,447

(22) PCT Filed: Nov. 12, 2015

(86) PCT No.: PCT/US2015/060314

§ 371 (c)(1),
(2) Date: May 12, 2017

(87) PCT Pub. No.: WO2016/077540

PCT Pub. Date: May 19, 2016

(65) Prior Publication Data

US 2017/0335322 A1 Nov. 23, 2017

Related U.S. Application Data

(60) Provisional application No. 62/078,911, filed on Nov. 12, 2014.

(51) Int. Cl.

| | |
|---|---|
| ***C12N 15/11*** | (2006.01) |
| ***C12N 15/113*** | (2010.01) |
| ***A61K 31/12*** | (2006.01) |
| ***A61K 31/7125*** | (2006.01) |
| ***C12N 15/00*** | (2006.01) |
| ***A61K 45/06*** | (2006.01) |
| ***A61K 31/192*** | (2006.01) |
| ***A61K 31/235*** | (2006.01) |
| ***A61K 31/405*** | (2006.01) |
| ***A61K 31/232*** | (2006.01) |
| ***A61K 31/7076*** | (2006.01) |
| ***A61K 31/713*** | (2006.01) |

(52) U.S. Cl.

CPC ............ *C12N 15/113* (2013.01); *A61K 31/12* (2013.01); *A61K 31/192* (2013.01); *A61K 31/232* (2013.01); *A61K 31/235* (2013.01); *A61K 31/405* (2013.01); *A61K 31/7076* (2013.01); *A61K 31/713* (2013.01); *A61K 31/7125* (2013.01); *A61K 45/06* (2013.01); *C12N 15/00* (2013.01); *C12N 2310/14* (2013.01); *C12N 2310/321* (2013.01); *C12N 2310/341* (2013.01); *C12N 2320/31* (2013.01)

(58) Field of Classification Search

CPC .. A61K 38/00; A61K 31/713; A61K 2300/00; C12N 15/113

See application file for complete search history.

(56) References Cited

U.S. PATENT DOCUMENTS

| | | | |
|---|---|---|---|
| 3,687,808 | A | 8/1972 | Merigan et al. |
| 4,845,205 | A | 7/1989 | Huynh Dinh et al. |
| 5,130,302 | A | 7/1992 | Spielvogel et al. |
| 5,134,066 | A | 7/1992 | Rogers et al. |
| 5,175,273 | A | 12/1992 | Bischofberger et al. |
| 5,367,066 | A | 11/1994 | Urdea et al. |
| 5,432,272 | A | 7/1995 | Benner |
| 5,457,187 | A | 10/1995 | Gmeiner et al. |
| 5,459,255 | A | 10/1995 | Cook et al. |
| 5,484,908 | A | 1/1996 | Froehler et al. |
| 5,502,177 | A | 3/1996 | Matteucci et al. |
| 5,525,711 | A | 6/1996 | Hawkins et al. |
| 5,552,540 | A | 9/1996 | Hamlambidis |
| 5,587,469 | A | 12/1996 | Cook et al. |
| 5,594,121 | A | 1/1997 | Froehler et al. |
| 5,596,091 | A | 1/1997 | Switzer |
| 5,614,617 | A | 3/1997 | Cook et al. |
| 5,645,985 | A | 7/1997 | Froehler et al. |

(Continued)

FOREIGN PATENT DOCUMENTS

| | | |
|---|---|---|
| WO | WO 2008/150729 | 12/2008 |
| WO | WO 2008/154401 | 12/2008 |

(Continued)

OTHER PUBLICATIONS

Frieden et al., "Expanding the design horizon of antisense oligonucleotides with alpha-L-LNA" Nucleic Acids Research (2003) 21: 6365-6372.

(Continued)

*Primary Examiner* — Dana H Shin

(74) *Attorney, Agent, or Firm* — Parker Highlander, PLLC

(57) ABSTRACT

In certain embodiments, hybridization results in modulation of the amount activity or expression of the target nucleic acid in a cell. In certain embodiments, the target nucleic acid is a nucleic acid that encodes cartilage oligomeric matrix protein. In certain embodiments, the target nucleic acid is a nucleic acid expressed in the growth plate, tendon, or cartilage.

16 Claims, No Drawings

Specification includes a Sequence Listing.

(56) References Cited

U.S. PATENT DOCUMENTS

| | | | | |
|---|---|---|---|---|
| 5,681,941 | A | 10/1997 | Cook et al. | |
| 5,750,692 | A | 5/1998 | Cook et al. | |
| 5,763,588 | A | 6/1998 | Matteucci et al. | |
| 5,830,653 | A | 11/1998 | Froehler et al. | |
| 6,005,096 | A | 12/1999 | Matteucci et al. | |
| 7,399,845 | B2 | 7/2008 | Seth et al. | |
| 7,427,672 | B2 | 9/2008 | Imanishi et al. | |
| 2003/0077609 | A1* | 4/2003 | Jakobsen | C07H 21/00 435/6.11 |
| 2004/0023241 | A1* | 2/2004 | Alsobrook, II | C07K 14/47 435/6.14 |
| 2004/0171570 | A1 | 9/2004 | Allerson | |
| 2005/0246794 | A1* | 11/2005 | Khvorova | A61K 31/713 800/286 |
| 2007/0134655 | A1 | 6/2007 | Bentwich | |
| 2008/0146788 | A1* | 6/2008 | Bhat | C12N 15/111 536/24.5 |
| 2015/0126586 | A1* | 5/2015 | Adamsky | C12N 15/113 514/44 A |

FOREIGN PATENT DOCUMENTS

| | | |
|---|---|---|
| WO | WO 2009/006478 | 1/2009 |
| WO | WO 2010/135322 | 11/2010 |
| WO | WO 2011/123394 | 10/2011 |

OTHER PUBLICATIONS

Inui et al. "Identification and Characterization of Cartilage Oligomeric Matrix Protein as a Novel Pathogenic Factor in Keloids" Am J Pathol. (2011) 179(4): 1951-1960.

Posey et al. "RNAi Reduces Expression and Intracellular Retention of Mutant Cartilage Oligomeric Matrix Protein" PLoS ONE (2010) 5(4): e10302 1-9.

Posey et al., "An inducible cartilage oligomeric matrix protein mouse model recapitulates human pseudoachondroplasia phenotype" Am. J. Pathol. (2009) 175: 1555-1563.

Posey et al., "The role of cartilage oligomeric matrix protein (COMP) in skeletal disease," Curr. Drug Targets. (2008) 9(10): 869-77.

International search report for PCT/US15/60314 dated Feb. 12, 2016.

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74: 118-134.

* cited by examiner

COMPOUNDS AND METHODS FOR THE MODULATION OF COMP

STATEMENT OF GOVERNMENT SUPPORT

This invention was made with government support under 5R01AR057117-05 awarded by National Institute of Health. The U.S. government has certain rights in the invention.

SEQUENCE LISTING

The present application is being filed along with a Sequence Listing in electronic format. The Sequence Listing is provided as a file entitled CORE0125USASEQ_ST25.txt, created May 11, 2017, which is 64 Kb in size. The information in the electronic format of the sequence listing is incorporated herein by reference in its entirety.

BACKGROUND

Cartilage oligomeric matrix protein is a non-collagenous extracellular matrix protein expressed in cartilage, ligament, and tendon and encoded by the COMP gene. Mutations in the COMP gene cause the skeletal dysplasias pseudoachondroplasia and multiple epiphyseal dysplasia. See, for example, Posey, K L: "The role of cartilage oligomeric matrix protein (COMP) in skeletal disease," Curr. Drug Targets. 2008 October; 9(10):869-77. Pseudoachondroplasia is an inhereited bone growth disorder. Individuals having pseudoachondroplasia generally have a short stature with the average height of both males and females under 48 inches. Additionally, individuals with pseudoachondroplasia experience joint pain in adolescence that progresses to osteoarthritis in adulthood. Multiple epiphyseal dysplasia affects the epiphyses, the ends of the long bones in the arms and legs. Symptoms of multiple epiphyseal dysplasia include joint pain, early-onset arthritis, and in some cases mild short stature and/or a waddling walk. Both dysplasias pseudoachondroplasia and multiple epiphyseal dysplasia stem from the intracellular retention of cartilage oligomeric matrix protein in the enlarged rough endoplasmic reticulum. The retention of cartilage oligomeric matrix protein causes chondrocyte cell death which decreases linear bone growth. The retention of cartilage oligomeric matrix protein also reduces the stability of the extracellular matrix, which causes abnormalities in the extracellular matrix and makes the extracellular matrix erode during normal physical activity. Additionally, increased serum cartilage levels of cartilage oligomeric matrix protein are found in patients with aggressive arthritis.

Antisense compounds have been used to modulate target nucleic acids. Antisense compounds comprising a variety of chemical modifications and motifs have been reported. In certain instances, such compounds are useful as research tools, diagnostic reagents, and as therapeutic agents. In certain instances antisense compounds have been shown to modulate protein expression by binding to a target messenger RNA (mRNA) encoding the protein. In certain instances, such binding of an antisense compound to its target mRNA results in cleavage of the mRNA. Antisense compounds that modulate processing of a pre-mRNA have also been reported. Such antisense compounds alter splicing, interfere with polyadenlyation or prevent formation of the 5'-cap of a pre-mRNA.

SUMMARY

Certain embodiments provide antisense compounds targeted to a COMP nucleic acid. In certain embodiments, the COMP nucleic acid has the sequence set forth in GENBANK Accession No. NM_000095.2 (incorporated herein as SEQ ID NO: 1).

In certain ebodiments, the present disclosure provides for modified oligonucleotides that reduce the expression of target nucleic acids in the growth plate, tendon, or cartilage. In certain embodiments, the present disclosure provides for modified oligonucleotides that reduce the expression of COMP in a cell or tissue. In certain embodiments, the present disclosure provides for modified oligonucleotides that reduce the expression of COMP in the growth plate, tendon, or cartilage. In certain embodiments, the present disclosure provides for modified oligonucleotides that reduce the expression of COMP in the growth plate, tendon, or cartilage and thereby ameliorate one or more symptoms of pseudoachondroplasia or multiple epiphyseal dysplasia.

The present disclosure provides the following non-limiting numbered embodiments:

Embodiment 1: A compound comprising a modified oligonucleotide consisting of 8 to 80 linked nucleosides complementary within nucleobases 43-58, 52-67, 74-89, 86-101, 98-113, 110-125, 252-267, 274-289, 300-315, 312-327, 335-350, 344-359, 356-371, 388-403, 402-417, 484-499, 500-515, 520-535, 536-551, 567-582, 591-606, 616-631, 635-650, 653-668, 671-686, 694-709, 728-743, 758-773, 770-785, 782-797, 816-831, 829-844, 846-861, 876-891, 902-917, 914-929, 975-990, 1026-1041, 1056-1071, 1081-1096, 1094-1109, 1124-1139, 1162-1177, 1174-1189, 1201-1216, 1269-1284, 1282-1297, 1317-1332, 1327-1342, 1336-1351, 1359-1374, 1387-1402, 1392-1407, 1462-1477, 1488-1503, 1525-1540, 1568-1583, 1704-1719, 1881-1896, 1920-1935, 1932-1947, 2004-2019, 2017-2032, 2073-2088, 2147-2162, 2189-2204, 2234-2249, 2246-2261, 2277-2292, 2289-2304, 2300-2315, 2316-2331, 1212-1227, 44-59, 55-70, 77-92, 89-104, 101-116, 1212-1227, 255-270, 277-292, 303-318, 314-329, 338-353, 347-362, 359-374, 391-406, 403-418, 489-504, 503-518, 523-538, 539-554, 582-597, 594-609, 626-641, 638-653, 662-677, 674-689, 697-712, 732-747, 761-776, 773-788, 786-801, 819-834, 832-847, 867-882, 888-903, 905-920, 966-981, 982-997, 1034-1049, 1059-1074, 1082-1097, 1098-1113, 1126-1141, 1165-1180, 1181-1196, 1228-1243, 1272-1287, 1284-1299, 1318-1333, 1328-1343, 1337-1352, 1363-1378, 1389-1404, 1396-1411, 1465-1480, 1504-1519, 1559-1574, 1571-1586, 1707-1722, 1895-1910, 1923-1938, 1953-1968, 2008-2023, 2037-2052, 2128-2143, 2150-2165, 2192-2207, 2237-2252, 2247-2262, 2281-2296, 2291-2306, 2306-2321, 2319-2334, 46-61, 58-73, 80-95, 92-107, 104-119, 246-261, 257-272, 280-295, 306-321, 329-344, 341-356, 350-365, 379-394, 396-411, 449-464, 493-508, 507-522, 529-544, 542-557, 585-600, 597-612, 629-644, 641-656, 665-680, 688-703, 700-715, 735-750, 764-779, 776-791, 789-804, 823-838, 836-851, 870-885, 891-906, 908-923, 969-984, 1017-1032, 1037-1052, 1062-1077, 1085-1100, 1107-1122, 1067-1082, 1168-1183, 1185-1200, 1232-1247, 1276-1291, 1308-1323, 1319-1334, 1330-1345, 1353-1368, 1380-1395, 1390-1405, 1459-1474, 1468-1483, 1519-1534, 1562-1577, 1574-1589, 1746-1761, 1898-1913, 1926-1941, 1956-1971, 2011-2026, 2040-2055, 2131-2146, 2166-2181, 2196-2211, 2240-2255, 2269-2284, 2284-2299, 2294-2309, 2308-2323, 2322-2337, 49-64, 62-77, 83-98, 95-110, 107-122, 249-264, 271-286, 297-312, 309-324, 332-347, 342-357, 353-368, 382-397, 399-414, 451-466, 497-512, 513-528, 533-548, 564-579, 588-603, 613-628, 632-647, 650-665, 668-683, 691-706, 725-740, 751-766, 767-782, 779-794, 813-828, 826-841, 839-854, 873-888, 894-909, 911-926, 972-987, 1020-1035, 1042-1057, 1065-1080, 1088-1103, 1109-1124, 1159-1174, 1171-1186, 1188-1203, 1234-1249, 1279-1294, 1313-1328, 1324-1339, 1333-1348, 1356-1371, 1383-1398, 1391-1406, 1460-1475, 1475-1490, 1522-1537, 1565-1580, 1647-1662, 1749-1764, 1917-1932, 1929-1944, 1974-1989, 2014-2029, 2070-2085, 2142-2157, 2169-2184, 2199-2214, 2243-2258, 2274-2289, 2287-2302, 2297-2312, 2313-2328, or 2325-2340 of SEQ ID NO: 1, wherein said modified oligonucleotide is at least 85%, 90%, 95%, or 100% complementary to SEQ ID NO: 1.

Embodiment 2: A compound comprising a modified oligonucleotide consisting of 8 to 80 linked nucleosides having a nucleobase sequence comprising a portion of at least 8 contiguous nucleobases 100% complementary to an equal length portion of nucleobases 43-58, 52-67, 74-89, 86-101, 98-113, 110-125, 252-267, 274-289, 300-315, 312-327, 335-350, 344-359, 356-371, 388-403, 402-417, 484-499, 500-515, 520-535, 536-551, 567-582, 591-606, 616-631, 635-650, 653-668, 671-686, 694-709, 728-743, 758-773, 770-785, 782-797, 816-831, 829-844, 846-861, 876-891, 902-917, 914-929, 975-990, 1026-1041, 1056-1071, 1081-1096, 1094-1109, 1124-1139, 1162-1177, 1174-1189, 1201-1216, 1269-1284, 1282-1297, 1317-1332, 1327-1342, 1336-1351, 1359-1374, 1387-1402, 1392-1407, 1462-1477, 1488-1503, 1525-1540, 1568-1583, 1704-1719, 1881-1896, 1920-1935, 1932-1947, 2004-2019, 2017-2032, 2073-2088, 2147-2162, 2189-2204, 2234-2249, 2246-2261, 2277-2292, 2289-2304, 2300-2315, 2316-2331, 1212-1227, 44-59, 55-70, 77-92, 89-104, 101-116, 1212-1227, 255-270, 277-292, 303-318, 314-329, 338-353, 347-362, 359-374, 391-406, 403-418, 489-504, 503-518, 523-538, 539-554, 582-597, 594-609, 626-641, 638-653, 662-677, 674-689, 697-712, 732-747, 761-776, 773-788, 786-801, 819-834, 832-847, 867-882, 888-903, 905-920, 966-981, 982-997, 1034-1049, 1059-1074, 1082-1097, 1098-1113, 1126-1141, 1165-1180, 1181-1196, 1228-1243, 1272-1287, 1284-1299, 1318-1333, 1328-1343, 1337-1352, 1363-1378, 1389-1404, 1396-1411, 1465-1480, 1504-1519, 1559-1574, 1571-1586, 1707-1722, 1895-1910, 1923-1938, 1953-1968, 2008-2023, 2037-2052, 2128-2143, 2150-2165, 2192-2207, 2237-2252, 2247-2262, 2281-2296, 2291-2306, 2306-2321, 2319-2334, 46-61, 58-73, 80-95, 92-107, 104-119, 246-261, 257-272, 280-295, 306-321, 329-344, 341-356, 350-365, 379-394, 396-411, 449-464, 493-508, 507-522, 529-544, 542-557, 585-600, 597-612, 629-644, 641-656, 665-680, 688-703, 700-715, 735-750, 764-779, 776-791, 789-804, 823-838, 836-851, 870-885, 891-906, 908-923, 969-984, 1017-1032, 1037-1052, 1062-1077, 1085-1100, 1107-1122, 1067-1082, 1168-1183, 1185-1200, 1232-1247, 1276-1291, 1308-1323, 1319-1334, 1330-1345, 1353-1368, 1380-1395, 1390-1405, 1459-1474, 1468-1483, 1519-1534, 1562-1577, 1574-1589, 1746-1761, 1898-1913, 1926-1941, 1956-1971, 2011-2026, 2040-2055, 2131-2146, 2166-2181, 2196-2211, 2240-2255, 2269-2284, 2284-2299, 2294-2309, 2308-2323, 2322-2337, 49-64, 62-77, 83-98, 95-110, 107-122, 249-264, 271-286, 297-312, 309-324, 332-347, 342-357, 353-368, 382-397, 399-414, 451-466, 497-512, 513-528, 533-548, 564-579, 588-603, 613-628, 632-647, 650-665, 668-683, 691-706, 725-740, 751-766, 767-782, 779-794, 813-828, 826-841, 839-854, 873-888, 894-909, 911-926, 972-987, 1020-1035, 1042-1057, 1065-1080, 1088-1103, 1109-1124, 1159-1174, 1171-1186, 1188-1203, 1234-1249, 1279-1294, 1313-1328, 1324-1339, 1333-1348, 1356-1371, 1383-1398, 1391-1406, 1460-1475, 1475-1490, 1522-1537, 1565-1580, 1647-1662, 1749-1764, 1917-1932, 1929-1944, 1974-1989, 2014-2029, 2070-2085, 2142-2157, 2169-2184, 2199-2214, 2243-2258, 2274-2289, 2287-2302, 2297-2312, 2313-2328, or 2325-2340 of SEQ ID NO:1, wherein the nucleobase sequence of the modified oligonucleotide is at least 85%, 90%, 95%, or 100% complementary to SEQ ID NO: 1.

Embodiment 3: A compound comprising a modified oligonucleotide consisting of 8 to 80 linked nucleosides having a nucleobase sequence comprising a portion of at least 8 contiguous nucleobases complementary to an equal length portion of nucleobases 43-58, 52-67, 74-89, 86-101, 98-113, 110-125, 252-267, 274-289, 300-315, 312-327, 335-350, 344-359, 356-371, 388-403, 402-417, 484-499, 500-515, 520-535, 536-551, 567-582, 591-606, 616-631, 635-650, 653-668, 671-686, 694-709, 728-743, 758-773, 770-785, 782-797, 816-831, 829-844, 846-861, 876-891, 902-917, 914-929, 975-990, 1026-1041, 1056-1071, 1081-1096, 1094-1109, 1124-1139, 1162-1177, 1174-1189, 1201-1216, 1269-1284, 1282-1297, 1317-1332, 1327-1342, 1336-1351, 1359-1374, 1387-1402, 1392-1407, 1462-1477, 1488-1503, 1525-1540, 1568-1583, 1704-1719, 1881-1896, 1920-1935, 1932-1947, 2004-2019, 2017-2032, 2073-2088, 2147-2162, 2189-2204, 2234-2249, 2246-2261, 2277-2292, 2289-2304, 2300-2315, 2316-2331, 1212-1227, 44-59, 55-70, 77-92, 89-104, 101-116, 1212-1227, 255-270, 277-292, 303-318, 314-329, 338-353, 347-362, 359-374, 391-406, 403-418, 489-504, 503-518, 523-538, 539-554, 582-597, 594-609, 626-641, 638-653, 662-677, 674-689, 697-712, 732-747, 761-776, 773-788, 786-801, 819-834, 832-847, 867-882, 888-903, 905-920, 966-981, 982-997, 1034-1049, 1059-1074, 1082-1097, 1098-1113, 1126-1141, 1165-1180, 1181-1196, 1228-1243, 1272-1287, 1284-1299, 1318-1333, 1328-1343, 1337-1352, 1363-1378, 1389-1404, 1396-1411, 1465-1480, 1504-1519, 1559-1574, 1571-1586, 1707-1722, 1895-1910, 1923-1938, 1953-1968, 2008-2023, 2037-2052, 2128-2143, 2150-2165, 2192-2207, 2237-2252, 2247-2262, 2281-2296, 2291-2306, 2306-2321, 2319-2334, 46-61, 58-73, 80-95, 92-107, 104-119, 246-261, 257-272, 280-295, 306-321, 329-344, 341-356, 350-365, 379-394, 396-411, 449-464, 493-508, 507-522, 529-544, 542-557, 585-600, 597-612, 629-644, 641-656, 665-680, 688-703, 700-715, 735-750, 764-779, 776-791, 789-804, 823-838, 836-851, 870-885, 891-906, 908-923, 969-984, 1017-1032, 1037-1052, 1062-1077, 1085-1100, 1107-1122, 1067-1082, 1168-1183, 1185-1200, 1232-1247, 1276-1291, 1308-1323, 1319-1334, 1330-1345, 1353-1368, 1380-1395, 1390-1405, 1459-1474, 1468-1483, 1519-1534, 1562-1577, 1574-1589, 1746-1761, 1898-1913, 1926-1941, 1956-1971, 2011-2026, 2040-2055, 2131-2146, 2166-2181, 2196-2211, 2240-2255, 2269-2284, 2284-2299, 2294-2309, 2308-2323, 2322-2337, 49-64, 62-77, 83-98, 95-110, 107-122, 249-264, 271-286, 297-312, 309-324, 332-347, 342-357, 353-368, 382-397, 399-414, 451-466, 497-512, 513-528, 533-548, 564-579, 588-603, 613-628, 632-647, 650-665, 668-683, 691-706, 725-740, 751-766, 767-782, 779-794, 813-828, 826-841, 839-854, 873-888, 894-909, 911-926, 972-987, 1020-1035, 1042-1057, 1065-1080, 1088-1103, 1109-1124, 1159-1174, 1171-1186, 1188-1203, 1234-1249, 1279-1294, 1313-1328, 1324-1339, 1333-1348, 1356-1371, 1383-1398, 1391-1406, 1460-1475, 1475-1490, 1522-1537, 1565-1580, 1647-1662, 1749-1764, 1917-1932, 1929-1944, 1974-1989, 2014-2029, 2070-2085, 2142-2157, 2169-2184, 2199-2214, 2243-2258, 2274-2289, 2287-2302, 2297-2312, 2313-2328, or 2325-2340 of a COMP nucleic acid having the nucleobase sequence of SEQ ID NO: 1, wherein the nucleobase sequence of the modified oligonucleotide is complementary to SEQ ID NO:1.

Embodiment 4: A compound comprising a modified oligonucleotide consisting of 8 to 80 linked nucleosides complementary within nucleotides 902-917, 2316-2331, 1559-1574, 2319-2334, 1062-1077, 1067-1082, 1276-1291, 1353-1368, 2240-2255, 2322-2337, 1324-1339, 2325-2340, 1212-1227, 789-804, 908-923, 1232-1247, 1459-1474, 1519-1534, 1956-1971, 2269-2284, 2308-2323, 564-579, 1042-1057, 1065-1080, 1279-1294, 1391-1406, 1460-1475, 1917-1932, 2070-2085, 2274-2289, 484-499, 591-606, 594-609, 888-903, 1181-1196, 1284-1299, 1318-1333, 1328-1343, 1389-1404, 1396-1411, 1571-1586, 2150-2165, 2319-2334, 597-612, 891-906, 1037-1052, 1107-1122, 1380-1395, 1574-1589, 356-371, 567-582, 758-773, 816-831, 829-844, 1094-1109, 1201-1216, 1269-1284, 1282-1297, 1327-1342, 1392-1407, 1568-1583, 1704-1719, 1920-1935, 1932-1947, 2073-2088, 2277-2292, 1212-1227, or 2319-2334 of SEQ ID NO: 1.

Embodiment 5: A compound comprising a modified oligonucleotide consisting of 8 to 80 linked nucleosides having a nucleobase sequence comprising any one of SEQ ID NO: 39, 76, 132, 148, 187, 190, 194, 198, 215, 220, 268, 292, 77, 178, 183, 193, 201, 203, 209, 216, 219, 239, 258, 259, 266, 272, 273, 278, 283, 288, 20, 25, 97, 110, 120, 123, 124, 125, 128, 129, 133, 141, 148, 169, 182, 186, 189, 199, 205, 17, 24, 32, 35, 36, 45, 49, 49, 50, 51, 53, 57, 61, 62, 64, 65, 68, 73, 77, or 148.

Embodiment 6: A compound comprising a modified oligonucleotide having a nucleobase sequence consisting of of SEQ ID NO: 148.

Embodiment 7: A compound comprising a modified oligonucleotide consisting of 10 to 30 linked nucleosides and having a nucleobase sequence comprising at least 8 contiguous nucleobases of any of the nucleobase sequences of SEQ ID NOs: 5-292.

Embodiment 8: A compound comprising a modified oligonucleotide consisting of 10 to 30 linked nucleosides and having a nucleobase sequence comprising at least 9 contiguous nucleobases of any of the nucleobase sequences of SEQ ID NOs: 5-292.

Embodiment 9: A compound comprising a modified oligonucleotide consisting of 10 to 30 linked nucleosides and having a nucleobase sequence comprising at least 10 contiguous nucleobases of any of the nucleobase sequences of SEQ ID NOs: 5-292.

Embodiment 10: A compound comprising a modified oligonucleotide consisting of 10 to 30 linked nucleosides and having a nucleobase sequence comprising at least 11 contiguous nucleobases of any of the nucleobase sequences of SEQ ID NOs: 5-292.

Embodiment 11: A compound comprising a modified oligonucleotide consisting of 10 to 30 linked nucleosides and having a nucleobase sequence comprising at least 12 contiguous nucleobases of any of the nucleobase sequences of SEQ ID NOs: 5-292.

Embodiment 12: A compound comprising a modified oligonucleotide consisting of 10 to 30 linked nucleosides and having a nucleobase sequence comprising the nucleobase sequence of any one of SEQ ID NOs: 6-808.

Embodiment 13: A compound comprising a modified oligonucleotide consisting of the nucleobase sequence of any one of SEQ ID NOs: 5-292.

Embodiment 14: A compound comprising a modified oligonucleotide having a nucleobase sequence comprising at least an 8 nucleobase portion of any one of SEQ ID NOs: 39, 76, 132, 148, 187, 190, 194, 198, 215, 220, 268, 292, 77, 178, 183, 193, 201, 203, 209, 216, 219, 239, 258, 259, 266, 272, 273, 278, 283, 288, 20, 25, 97, 110, 120, 123, 124, 125, 128, 129, 133, 141, 148, 169, 182, 186, 189, 199, 205, 17, 24, 32, 35, 36, 45, 49, 49, 50, 51, 53, 57, 61, 62, 64, 65, 68, 73, 77, or 148.

Embodiment 15: A compound comprising a modified oligonucleotide consisting of 10 to 30 linked nucleosides having a nucleobase sequence comprising any one of SEQ ID NOs: 5-292, wherein the modified oligonucleotide comprises:

a gap segment consisting of linked deoxynucleosides;

a 5' wing segment consisting of linked nucleosides; and a 3' wing segment consisting of linked nucleosides;

wherein the gap segment is positioned between the 5' wing segment and the 3' wing segment and wherein each nucleoside of each wing segment comprises a modified sugar.

Embodiment 16: A compound comprising a modified oligonucleotide consisting of 16 linked nucleosides having a nucleobase sequence consisting of the sequence recited in SEQ ID NO: 5-292, wherein the modified oligonucleotide comprises a gap segment consisting of ten linked deoxynucleosides;

a 5' wing segment consisting of three linked nucleosides; and a 3' wing segment consisting of three linked nucleosides;

wherein the gap segment is positioned between the 5' wing segment and the 3' wing segment, wherein each nucleoside of each wing segment comprises a cEt sugar; wherein each internucleoside linkage is a phosphorothioate linkage and wherein each cytosine is a 5-methylcytosine.

Embodiment 17: A compound comprising a modified oligonucleotide, wherein the modified oligonucleotide has a nucleobase sequence comprising the sequence recited in SEQ ID NO: 148, wherein the modified oligonucleotide comprises a gap segment consisting of ten linked deoxynucleosides;

a 5' wing segment consisting of three linked nucleosides; and a 3' wing segment consisting of three linked nucleosides;

wherein the gap segment is positioned between the 5' wing segment and the 3' wing segment;

wherein each nucleoside of each wing segment comprises a cEt sugar; wherein each internucleoside linkage is a phosphorothioate linkage; and wherein each cytosine is a 5-methylcytosine.

Embodiment 18: The compound of any one of embodiments 1-17, wherein the oligonucleotide is at least 80%, 85%, 90%, 95% or 100% complementary to SEQ ID NO: 1.

Embodiment 19: The compound of any one of embodiments 1-18, wherein the modified oligonucleotide comprises at least one modified internucleoside linkage, at least one modified sugar, or at least one modified nucleobase.

Embodiment 20: The compound of embodiment 19, wherein the modified internucleoside linkage is a phosphorothioate internucleoside linkage.

Embodiment 21: The compound of embodiment 19 or 20, wherein the modified sugar is a bicyclic sugar.

Embodiment 22: The compound of embodiment 21, wherein the bicyclic sugar is selected from the group consisting of: 4'-$(CH_2)$—O-2' (LNA); 4'-$(CH_2)_2$—O-2' (ENA); and 4'-$CH(CH_3)$—O-2' (cEt).

Embodiment 23: The compound of embodiment 19 or 20, wherein the modified sugar is 2'-O-methoxyethyl.

Embodiment 24: The compound of any one of embodiments 19-23, wherein the modified nucleobase is a 5-methylcytosine.

Embodiment 25: The compound of any one of embodiments 1-24, wherein the modified oligonucleotide comprises:

(a) a gap segment consisting of linked deoxynucleosides;

(b) a 5' wing segment consisting of linked nucleosides; and (c) a 3' wing segment consisting of linked nucleosides;

wherein the gap segment is positioned immediately adjacent to and between the 5' wing segment and the 3' wing segment and wherein each nucleoside of each wing segment comprises a modified sugar.

Embodiment 26: The compound of any one of embodiments 1-25, wherein the compound is single-stranded.

Embodiment 27: The compound of any one of embodiments 1-25, wherein the compound is double-stranded.

Embodiment 28: The compound of any one of embodiments 1-27, wherein the compound comprises ribonucleotides.

Embodiment 29: The compound of any one of embodiments 1-27, wherein the compound comprises deoxyribonucleotides.

Embodiment 30: The compound of any one of embodiments 1-29, wherein the modified oligonucleotide consists of 10 to 30 linked nucleosides.

Embodiment 31: The compound of any one of embodiments 1-29, wherein the modified oligonucleotide consists of 12 to 30 linked nucleosides.

Embodiment 32: The compound of any one of embodiments 1-29, wherein the modified oligonucleotide consists of 15 to 30 linked nucleosides.

Embodiment 33: The compound of any one of embodiments 1-32, wherein the modified oligonucleotide is an antisense oligonucleotide.

Embodiment 34: A composition comprising the compound of any one of embodiments 1-33 or salt thereof and a pharmaceutically acceptable carrier.

Embodiment 35: A method of reducing target RNA in a cell, comprising contacting a cell with the compound of any of embodiments 1 to 33 or the composition of embodiment 33, and thereby reducing target RNA.

Embodiment 36: A method of inhibiting expression of cartilage oligomeric matrix protein in a cell, comprising administering to the subject a compound of any of embodiments 1 to 33 or the composition of embodiment 33, and thereby reducing experession of cartilage oligomeric matrix protein in a cell.

Embodiment 37: The method of embodiment 35 or 36, wherein the cell is a growth plate cell.

Embodiment 38: The method of embodiment 35 or 36, wherein the cell is a tendon cell.

Embodiment 39: The method of embodiment 35 or 36, wherein the cell is a cartilage cell.

Embodiment 40: The method of any of embodiments 35 to 39, whrein the cell is in vitro.

Embodiment 41: The method of any of embodiments 35 to 39, whrein the cell is in an animal.

Embodiment 42: The method of embodiment 41, wherein the animal is a human.

Embodiment 43: The method of any of embodiments 35 to 42, wherein the target RNA is COMP RNA.

Embodiment 44: A method of treating, preventing, or ameliorating a disease associated with retention of cartilage oligomeric matrix protein in the enlarged rough endoplasmic reticulum in a subject comprising administering to the subject a compound of any of embodiments 1 to 32 or the composition of embodiment 33, and thereby treating, preventing, or ameliorating the disease.

Embodiment 45: The method of embodiment 44, wherein the disease is pseudoachondroplasia.

Embodiment 46: The method of embodiment 44, wherein the disease is multiple epiphyseal dysplasia.

Embodiment 47: Use of a compound of any of embodiments 1 to 33 or the composition of embodiment 34 for the treatment of a disease associated with retention of cartilage oligomeric matrix protein.

Embodiment 48: Use of a compound of any of embodiments 1 to 33 or the composition of embodiment 34 for the preparation of a medicament for the treatment of a disease associated with retention of cartilage oligomeric matrix protein.

Embodiment 49: The use of embodiment 47 or 48, wherein the disease is pseudoachondroplasia.

Embodiment 50: The use of embodiment 47 or 48, wherein the disease is multiple epiphyseal dysplasia.

Embodiment 51: The method of any of embodiments 36-39 or 41-46, wherein the administration is intramuscular.

Embodiment 52: The method of any of embodiments 36-39 or 41-46, wherein the administration is subcutaneous.

Embodiment 53: The method of any of embodiments 36-39 or 41-46, wherein the administration is intraperitoneal.

Embodiment 54: The method of any of embodiments 36-39, 41-46, or 51-53, wherein inflammation in cartilage of the subject is reduced.

Embodiment 55: The method of any of embodiments 44-46 or 51-54, wherein retention of cartilage oligomeric matrix protein in the roughendoplasmic reticulum in the subject is reduced.

Embodiment 56: The method of any of embodiments 44-46 or 51-55 comprising administering to the subject a second compound or pharmaceutical composition.

Embodiment 57: The method of embodiment 56, wherein the second compound or pharmaceutical composition comprises an anti-inflammatory compound.

Embodiment 58: The method of embodiment 56, wherein the second compound or pharmaceutical composition comprises an antioxidant compound.

Embodiment 59: The method of embodiment 57, wherein the second compound or pharmaceutical composition comprises Indometacin or Indomethacin.

Embodiment 60: The method of embodiment 57, wherein the second compound or pharmaceutical composition comprises Ibuprofen.

Embodiment 61: The method of embodiment 57, wherein the second compound or pharmaceutical composition comprises Naproxen.

Embodiment 62: The method of embodiment 57 or 58, wherein the second compound or pharmaceutical composition comprises Lovaza.

Embodiment 63: The method of embodiment 58, wherein the second compound or pharmaceutical composition comprises Cordycepin.

Embodiment 64: The method of embodiment 57, wherein the second compound or pharmaceutical composition comprises Diacerein.

Embodiment 65: Use of a compound of any of embodiments 1 to 33 or the composition of embodiment 34 in combination with a second compound or composition for the treatment of a disease associated with retention of cartilage oligomeric matrix protein.

Embodiment 66: The use of embodiment 65, wherein the second compound or composition comprises an anti-inflammatory agent or an antioxidant.

Embodiment 67: The use of embodiment 65 or 66, wherein the second compound comprises Indometacin or Indomethacin.

Embodiment 68: The use of embodiment 65 or 66, wherein the second compound comprises Ibuprofen.

Embodiment 69: The use of embodiment 65 or 66, wherein the second compound comprises Naproxen.

Embodiment 70: The use of embodiment 65 or 66, wherein the second compound comprises Lovaza.

Embodiment 71: The use of embodiment 65 or 66, wherein the second compound comprises Cordycepin.

Embodiment 72: The use of embodiment 65 or 66, wherein the second compound comprises Diacerein.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

Unless otherwise indicated, the following terms have the following meanings:

As used herein, "cartilage oligomeric matrix protein" means any protein encoded by a COMP nucleic acid. In certain embodiments, the COMP nucleic acid has the sequence set forth in GENBANK Accession No. NM_000095.2 (incorporated herein as SEQ ID NO: 1).

As used herein, "COMP nucleic acid" means any nucleic acid encoding COMP. For example, in certain embodiments, a COMP nucleic acid includes a DNA sequence encoding COMP, an RNA sequence transcribed from DNA encoding COMP (including genomic DNA comprising introns and exons), including a non-protein encoding (i.e. non-coding) RNA sequence, and an mRNA sequence encoding COMP.

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. Chemical modifications of oligonucleotides include nucleoside modifications (including sugar moiety modifications and nucleobase modifications) and internucleoside linkage modifications. In reference to an oligonucleotide, chemical modification does not include differences only in nucleobase sequence.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety or a sugar surrogate.

As used herein, "substituted sugar moiety" means a furanosyl that is not a naturally occurring sugar moiety. Substituted sugar moieties include, but are not limited to furanosyls comprising substituents at the 2'-position, the 3'-position, the 5'-position and/or the 4'-position. Certain substituted sugar moieties are bicyclic sugar moieties.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means $—OCH_2CH_2OCH_3$.

As used herein, "2'-F nucleoside" refers to a nucleoside comprising a sugar comprising fluoroine at the 2' position. Unless otherwise indicated, the fluorine in a 2'-F nucleoside is in the ribo position (replacing the OH of a natural ribose).

As used herein, "2'-(ara)-F" refers to a 2'-F substituted nucleoside, wherein the fluoro group is in the arabino position.

As used herein the term "sugar surrogate" means a structure that does not comprise a furanosyl and that is capable of replacing the naturally occurring sugar moiety of a nucleoside, such that the resulting nucleoside sub-units are capable of linking together and/or linking to other nucleosides to form an oligomeric compound which is capable of hybridizing to a complementary oligomeric compound. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-$CH(CH_3)$—O-2' bridge.

As used herein, "locked nucleic acid nucleoside" or "LNA" means a nucleoside comprising a bicyclic sugar moiety comprising a 4'-$CH_2$—O-2' bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "RNA-like nucleoside" means a modified nucleoside that adopts a northern configuration and functions like RNA when incorporated into an oligonucleotide. RNA-like nucleosides include, but are not limited to 3'-endo furanosyl nucleosides and RNA surrogates.

As used herein, "3'-endo-furanosyl nucleoside" means an RNA-like nucleoside that comprises a substituted sugar moiety that has a 3'-endo conformation. 3'-endo-furanosyl nucleosides include, but are not limitied to: 2'-MOE, 2'-F, 2'-OMe, LNA, ENA, and cEt nucleosides.

As used herein, "RNA-surrogate nucleoside" means an RNA-like nucleoside that does not comprise a furanosyl. RNA-surrogate nucleosides include, but are not limited to hexitols and cyclopentanes.

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage. Examples of modified oligonucleotides include single-stranded and double-stranded compounds, such as, antisense oligonucleotides, siRNAs, shRNAs, ssRNAs, and occupancy-based compounds.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, an oligomeric compound comprises an oligonucleotide. In certain embodiments, an oligomeric compound consists of an oligonucleotide.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means a compound comprising two molecules that are covalently linked. In certain embodiments, a conjugate comprises an antibody and a modified oligonucleotide.

As used herein, "conjugate group" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measureable activity" means a measurable activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound is intended to hybridize.

As used herein, "non-target nucleic acid" means a nucleic acid molecule to which hybridization of an antisense compound is not intended or desired. In certain embodiments, antisense compounds do hybridize to a non-target, due to homology between the target (intended) and non-target (un-intended).

As used herein, "mRNA" means an RNA molecule that encodes a protein.

As used herein, "pre-mRNA" means an RNA transcript that has not been fully processed into mRNA. Pre-RNA includes one or more intron.

As used herein, "object RNA" means an RNA molecule other than a target RNA, the amount, activity, splicing, and/or function of which is modulated, either directly or indirectly, by a target nucleic acid. In certain embodiments, a target nucleic acid modulates splicing of an object RNA. In certain such embodiments, an antisense compound modulates the amount or activity of the target nucleic acid, resulting in a change in the splicing of an object RNA and ultimately resulting in a change in the activity or function of the object RNA.

As used herein, "microRNA" means a naturally occurring, small, non-coding RNA that represses gene expression of at least one mRNA. In certain embodiments, a microRNA represses gene expression by binding to a target site within a 3' untranslated region of an mRNA. In certain embodiments, a microRNA has a nucleobase sequence as set forth in miRBase, a database of published microRNA sequences found at http://microrna.sanger.ac.uk/sequences/. In certain embodiments, a microRNA has a nucleobase sequence as set forth in miRBase version 12.0 released September 2008, which is herein incorporated by reference in its entirety.

As used herein, "microRNA mimic" means an oligomeric compound having a sequence that is at least partially identical to that of a microRNA. In certain embodiments, a microRNA mimic comprises the microRNA seed region of a microRNA. In certain embodiments, a microRNA mimic modulates translation of more than one target nucleic acids. In certain embodiments, a microRNA mimic is double-stranded.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "mismatch" means a nucleobase of a first oligomeric compound that is not capable of pairing with a nucleobase at a corresponding position of a second oligomeric compound, when the first and second oligomeric compound are aligned. Either or both of the first and second oligomeric compounds may be oligonucleotides.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, a fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "modification motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified.

Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substuent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl ($—C(O)R_{aa}$), carboxyl ($—C(O)O—R_{aa}$), aliphatic groups, alicyclic groups, alkoxy, substituted oxy ($—O—R_{aa}$), aryl, aralkyl, heterocyclic radical, heteroaryl, heteroarylalkyl, amino ($—N(R_{bb})(R_{cc})$), imino ($\forall NR_{bb}$), amido ($—C(O)N(R_{bb})(R_{cc})$ or $—N(R_{bb})C(O)R_{aa}$), azido ($—N_3$), nitro ($—NO_2$), cyano ($—CN$), carbamido ($—OC(O)N(R_{bb})(R_{cc})$ or $—N(R_{bb})C(O)OR_{aa}$), ureido ($—N(R_{bb})C(O)N(R_{bb})(R_{cc})$), thioureido ($—N(R_{bb})C(S)N(R_{bb})—(R_{cc})$), guanidinyl ($—N(R_{bb})C(=NR_{bb})N(R_{bb})(R_{cc})$), amidinyl ($—C(=NR_{bb})N(R_{bb})(R_{cc})$ or $—N(R_{bb})C(=NR_{bb})(R_{aa})$), thiol ($—SR_{bb}$), sulfinyl ($—S(O)R_{bb}$), sulfonyl ($—S(O)_2R_{bb}$) and sulfonamidyl ($—S(O)_2N(R_{bb})(R_{cc})$ or $—N(R_{bb})S—(O)_2R_{bb}$). Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein, "Intracerebroventricular" or "ICV" means administration into the ventricular system of the brain.

Oligomeric Compounds

In certain embodiments, the present invention provides oligomeric compounds. In certain embodiments, such oligomeric compounds comprise oligonucleotides optionally comprising one or more conjugate and/or terminal groups. In certain embodiments, an oligomeric compound consists of an oligonucleotide. In certain embodiments, oligonucleotides comprise one or more chemical modifications. Such chemical modifications include modifications of one or more nucleoside (including modifications to the sugar moiety and/or the nucleobase) and/or modifications to one or more internucleoside linkage.

a. Certain Modified Nucleosides

In certain embodiments, provided herein are oligomeric compounds comprising or consisting of oligonuleotides comprising at least one modified nucleoside. Such modified nucleosides comprise a modified sugar moeity, a modified nucleobase, or both a modifed sugar moiety and a modified nucleobase.

i. Certain Sugar Moieties

In certain embodiments, oligomeric compounds of the invention comprise one or more modifed nucleosides comprising a modifed sugar moiety. Such oligomeric compounds comprising one or more sugar-modified nucleosides may have desirable properties, such as enhanced nuclease stability or increased binding affinity with a target nucleic acid relative to oligomeric compounds comprising only nucleosides comprising naturally occurring sugar moieties. In certain embodiments, modified sugar moieties are substitued sugar moieties. In certain embodiments, modified sugar moieties are bicyclic or tricyclic sugar moieties. In certain embodiments, modified sugar moieties are sugar surrogates. Such sugar surogates may comprise one or more substitutions corresponding to those of substituted sugar moieties.

In certain embodiments, modified sugar moieties are substituted sugar moieties comprising one or more substituent, including but not limited to substituents at the 2' and/or 5' positions. Examples of sugar substituents suitable for the 2'-position, include, but are not limited to: 2'-F, 2'-$OCH_3$ ("OMe" or "O-methyl"), and 2'-$O(CH_2)_2OCH_3$ ("MOE"). In certain embodiments, sugar substituents at the 2' position is selected from allyl, amino, azido, thio, O-allyl, O—$C_1$-$C_{10}$ alkyl, O—$C_1$-$C_{10}$ substituted alkyl; O—$C_1$-$C_{10}$ alkoxy;

O—$C_1$-$C_{10}$ substituted alkoxy, $OCF_3$, $O(CH_2)_2SCH_3$, $O(CH_2)_2$—O—N(Rm)(R4 and O—$CH_2$—C(=O)—N(Rm)(Rn), where each Rm and Rn is, independently, H or substituted or unsubstituted $C_1$-$C_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see,e.g., PCT International Application WO 2008/101157, for additional 5',2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, O—$C_1$-$C_{10}$ alkoxy; O—$C_1$-$C_{10}$ substituted alkoxy, SH, CN, OCN, $CF_3$, $OCF_3$, O-alkyl, S-alkyl, N($R_m$)-alkyl; O-alkenyl, S-alkenyl, or N($R_m$)-alkenyl; O-alkynyl, S-alkynyl, N($R_m$)-alkynyl; O-alkylenyl-O-alkyl, alkynyl, alkaryl, aralkyl, O-alkaryl, O-aralkyl, $O(CH_2)_2SCH_3$, O—$(CH_2)_2$—O—N($R_m$)($R_n$) or O—$CH_2$—C(=O)—N($R_m$)($R_n$), where each $R_m$ and $R_n$ is, independently, H, an amino protecting group or substituted or unsubstituted $C_1$-$C_{10}$ alkyl. These 2'-substituent groups can be further substituted with one or more substituent groups independently selected from hydroxyl, amino, alkoxy, carboxy, benzyl, phenyl, nitro ($NO_2$), thiol, thioalkoxy (S-alkyl), halogen, alkyl, aryl, alkenyl and alkynyl.

In certain embodiments, a 2'-substituted nucleoside comprises a 2'-substituent group selected from F, $NH_2$, $N_3$, $OCF_3$, O—$CH_3$, $O(CH_2)_3NH_2$, $CH_2$—CH=$CH_2$, O—$CH_2$—CH=$CH_2$, $OCH_2CH_2OCH_3$, $O(CH_2)_2SCH_3$, O—$(CH_2)_2$—O—N($R_m$)($R_n$), $O(CH_2)_2O(CH_2)_2N(CH_3)_2$, and N-substituted acetamide (O—$CH_2$—C(=O)—N($R_m$)($R_n$) where each $R_m$ and $R_n$ is, independently, H, an amino protecting group or substituted or unsubstituted $C_1$-$C_{10}$ alkyl.

In certain embodiments, a 2'-substituted nucleoside comprises a sugar moiety comprising a 2'-substituent group selected from F, $OCF_3$, O—$CH_3$, $OCH_2CH_2OCH_3$, $O(CH_2)_2$ $SCH_3$, O—$(CH_2)_2$—O—$N(CH_3)_2$, —$O(CH_2)_2O(CH_2)_2N(CH_3)_2$, and O—$CH_2$—C(=O)—N(H)$CH_3$.

In certain embodiments, a 2'-substituted nucleoside comprises a sugar moiety comprising a 2'-substituent group selected from F, O—$CH_3$, and $OCH_2CH_2OCH_3$.

Certain modifed sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —$[C(R_a)(R_b)]_n$—, —$[C(R_a)(R_b)]_n$—O—, —C($R_aR_b$)—N(R)—O— or, —C($R_aR_b$)—O—N(R)—; 4'-$CH_2$-2', 4'-$(CH_2)_2$-2',4'-$(CH_2)_3$-2', 4'-$(CH_2)$—O-2' (LNA); 4'-$(CH_2)$—S-2; 4'-$(CH_2)_2$ —O-2' (ENA); 4'-CH($CH_3$)—O-2' (cEt) and 4'-CH($CH_2OCH_3$)—O-2', and analogs thereof (see, e.g., U.S. Pat. No. 7,399,845, issued on Jul. 15, 2008); 4'-C($CH_3$)($CH_3$)—O-2' and analogs thereof, (see, e.g., WO2009/006478, published Jan. 8, 2009); 4'-$CH_2$—N($OCH_3$)-2' and analogs thereof (see, e.g., WO2008/150729, published Dec. 11, 2008); 4'-$CH_2$—O—N($CH_3$)-2' (see, e.g., US2004/0171570, published Sep. 2, 2004); 4'-$CH_2$—O—N(R)-2', and 4'-$CH_2$—N(R)—O-2'-, wherein each R is, independently, H, a protecting group, or $C_1$-$C_{12}$ alkyl; 4'-$CH_2$—N(R)—O-2', wherein R is H, $C_1$-$C_{12}$ alkyl, or a protecting group (see, U.S. Pat. No. 7,427,672, issued on Sep. 23, 2008); 4'-$CH_2$—C(H)($CH_3$)-2' (see, e.g., Chattopadhyaya, et al., *J. Org. Chem.,* 2009, 74, 118-134); and 4'-$CH_2$—C(=$CH_2$)-2' and analogs thereof (see, published PCT International Application WO 2008/154401, published on Dec. 8, 2008).

In certain embodiments, such 4' to 2' bridges independently comprise from 1 to 4 linked groups independently selected from —$[C(R_a)(R_b)]_n$—, —C($R_a$)=C($R_b$)—, —C($R_a$)=N—, —C(=$NR_a$)—, —C(=O)—, —C(=S)—, —O—, —Si$(R_a)_2$—, —S$(=O)_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S$(=O)_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-$CH_2$—O-2') BNA, (B) β-D-Methyleneoxy (4'-$CH_2$—O-2') BNA (also referred to as locked nucleic acid or LNA), (C) Ethyleneoxy (4'-$(CH_2)_2$—O-2') BNA, (D) Aminooxy (4'-$CH_2$—O—N(R)-2') BNA, (E) Oxyamino (4'-$CH_2$—N(R)—O-2') BNA, (F) Methyl(methyleneoxy) (4'-CH($CH_3$)—O-2') BNA (also referred to as constrained ethyl or cEt), (G) methylene-thio (4'-$CH_2$—S-2') BNA, (H) methylene-amino (4'-CH2-N(R)-2') BNA, (I) methyl carbocyclic (4'-$CH_2$—CH($CH_3$)-2') BNA, (J) propylene carbocyclic (4'-$(CH_2)_3$-2') BNA, and (M) 4'-$CH_2$—O—$CH_2$-2' as depicted below.

(A)

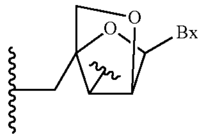

(B)

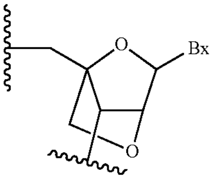

(C)

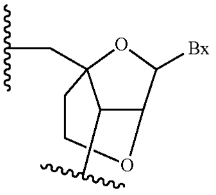

-continued (D)

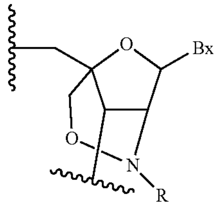

(E)

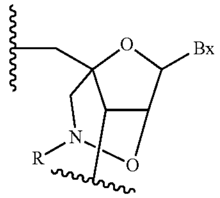

(F)

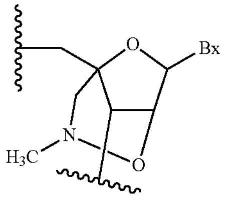

(G)

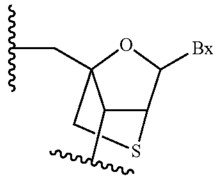

(H)

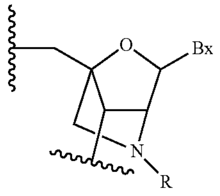

(I)

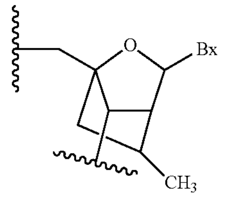

(M)

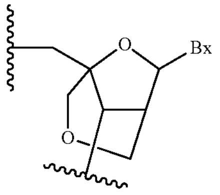

-continued (J)

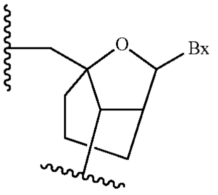

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.,* 1998, 4, 455-456; Koshkin et al., *Tetrahedron,* 1998, 54, 3607-3630; Wahlestedt et al., *Proc. Natl. Acad. Sci. U.S.A.,* 2000, 97, 5633-5638; Kumar et al., *Bioorg. Med. Chem. Lett.,* 1998, 8, 2219-2222; Singh et al., *J. Org. Chem.,* 1998, 63, 10035-10039; Srivastava et al., *J. Am. Chem. Soc.,* 129(26) 8362-8379 (Jul. 4, 2007); Elayadi et al., *Curr. Opinion Invens. Drugs,* 2001, 2, 558-561; Braasch et al., *Chem. Biol.,* 2001, 8, 1-7; Orum et al., *Curr. Opinion Mol. Ther.,* 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') bicyclic nucleosides have been incorporated into antisense oligonucleotides that showed antisense activity (Frieden et al., *Nucleic Acids Research,* 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occuring sugar is substituted, e.g., with a sulfer, carbon or nitrogen atom. In certain such embodiments, such modified sugar moiety also comprises bridging and/or non-bridging substituents as described above. For example, certain sugar surogates comprise a 4'-sulfer atom and a substitution at the 2'-position (see,e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research,* 1997, 25(22), 4429-4443 and Albaek et al., *J. Org. Chem.,* 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), and those compounds having Formula VII:

VII

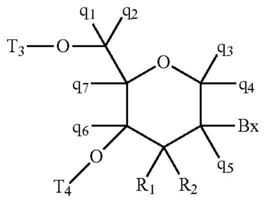

wherein independently for each of said at least one tetrahydropyran nucleoside analog of Formula VII:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclic and tricyclic sugar and sugar surrogate ring systems are known in the art that can be used to modify nucleosides (see, e.g., review article: Leumann, J. C, *Bioorganic & Medicinal Chemistry,* 2002, 10, 841-854).

In certain embodiments, sugar surrogates comprise rings having more than 5 atoms and more than one heteroatom. For example nucleosides comprising morpholino sugar moieties and their use in oligomeric compounds has been reported (see for example: Braasch et al., Biochemistry, 2002, 41, 4503-4510; and U.S. Pat. Nos. 5,698,685; 5,166,315; 5,185,444; and 5,034,506). As used here, the term “morpholino” means a sugar surrogate having the following structure:

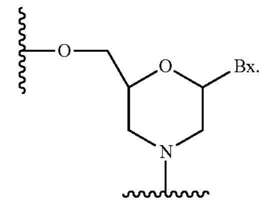

In certain embodiments, morpholinos may be modified, for example by adding or altering various substituent groups from the above morpholino structure. Such sugar surrogates are refered to herein as “modifed morpholinos.”

Combinations of modifications are also provided without limitation, such as 2'-F-5'-methyl substituted nucleosides (see PCT International Application WO 2008/101157 Published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

ii. Certain Modified Nucleobases

In certain embodiments, nucleosides of the present invention comprise one or more unmodified nucleobases. In certain embodiments, nucleosides of the present invention comprise one or more modifed nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($-C \equiv C-CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

b. Certain Internucleoside Linkages

In certain embodiments, nucleosides may be linked together using any internucleoside linkage to form oligonucleotides. The two main classes of internucleoside linking groups are defined by the presence or absence of a phosphorus atom. Representative phosphorus containing internucleoside linkages include, but are not limited to, phosphodiesters (P═O), phosphotriesters, methylphosphonates, phosphoramidate, and phosphorothioates (P═S). Representative non-phosphorus containing internucleoside linking groups include, but are not limited to, methylenemethylimino (—$CH_2$—$N(CH_3)$—O—$CH_2$—), thiodiester (—O—C(O)—S—), thionocarbamate (—O—C(O)(NH)—S—); siloxane (—O—$Si(H)_2$—O—); and N,N'-dimethylhydrazine (—$CH_2$—$N(CH_3)$—$N(CH_3)$—). Modified linkages, compared to natural phosphodiester linkages, can be used to alter, typically increase, nuclease resistance of the oligonucleotide. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-$CH_2$—$N(CH_3)$—O-5'), amide-3 (3'-$CH_2$—C(═O)—N(H)-5'), amide-4 (3'-$CH_2$—N(H)—C(═O)-5'), formacetal (3'-O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

i. 3'-Endo Modifications

In one aspect of the present disclosure, oligomeric compounds include nucleosides synthetically modified to induce a 3'-endo sugar conformation. A nucleoside can incorporate synthetic modifications of the heterocyclic base moiety, the sugar moiety or both to induce a desired 3'-endo sugar conformation. These modified nucleosides are used to mimic RNA like nucleosides so that particular properties of an oligomeric compound can be enhanced while maintaining the desirable 3'-endo conformational geometry. There is an apparent preference for an RNA type duplex (A form helix, predominantly 3'-endo) as a requirement of RNA interference which is supported in part by the fact that duplexes composed of 2'-deoxy-2'-F-nucleosides appear efficient in triggering RNAi response in the *C. elegans* system. Properties that are enhanced by using more stable 3'-endo nucleosides include but aren't limited to modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. The present invention provides oligomeric compounds having one or more nucleosides modified in such a way as to favor a C3'-endo type conformation.

Scheme 1

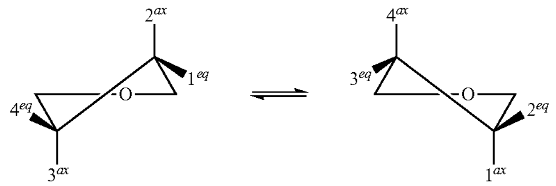

C2'-endo/Southern C3'-endo/Northern

Nucleoside conformation is influenced by various factors including substitution at the 2',3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2'deoxy-2'F-nucleosides (Kawasaki et al., J. Med. Chem. (1993), 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Some modifications actually lock the conformational geometry by formation of a bicyclic sugar moiety e.g. locked nucleic acid (LNA, Singh et al, Chem. Commun. (1998), 4, 455-456), and ethylene bridged nucleic acids (ENA, Morita et al, Bioorganic & Medicinal Chemistry Letters (2002), 12, 73-76.)

c. Certain Motifs

In certain embodiments, oligomeric compounds comprise or consist of oligonucleotides. In certain embodiments, such oligonucleotides comprise one or more chemical modification. In certain embodiments, chemically modified oligonucleotides comprise one or more modified sugars. In certain embodiments, chemically modified oligonucleotides comprise one or more modified nucleobases. In certain embodiments, chemically modified oligonucleotides comprise one or more modified internucleoside linkages. In certain embodiments, the chemical modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

i. Certain Sugar Motifs

In certain embodiments, oligonucleotides comprise one or more type of modified sugar moieties and/or naturally occurring sugar moieties arranged along an oligonucleotide or region thereof in a defined pattern or sugar motif Such sugar motifs include but are not limited to any of the sugar modifications discussed herein.

In certain embodiments, the oligonucleotides comprise or consist of a region having a gapmer sugar motif, which comprises two external regions or "wings" and a central or internal region or "gap." The three regions of a gapmer sugar motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric sugar gapmer). In certain embodiments, the sugar motifs of the 5'-wing differs from the sugar motif of the 3'-wing (asymmetric sugar gapmer).

ii. Certain Nucleobase Modification Motifs

In certain embodiments, oligonucleotides comprise chemical modifications to nucleobases arranged along the oligonucleotide or region thereof in a defined pattern or nucleobases modification motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, oligonucleotides comprise one or more nucleosides comprising a modified nucleobase. In certain embodiments, oligonucleotides having a gapmer sugar motif comprise a nucleoside comprising a modified nucleobase. In certain such embodiments, one nucleoside comprising a modified nucleobases is in the central gap of an oligonucleotide having a gapmer sugar motif. In certain embodiments, the sugar is an unmodified 2' deoxynucleoside. In certain embodiments, the modified nucleobase is selected from: a 2-thio pyrimidine and a 5-propyne pyrimidine In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

iii. Certain Nucleoside Motifs

In certain embodiments, oligonucleotides comprise nucleosides comprising modified sugar moieties and/or nucleosides comprising modified nucleobases. Such motifs can be described by their sugar motif and their nucleobase motif separately or by their nucleoside motif, which provides positions or patterns of modified nucleosides (whether modified sugar, nucleobase, or both sugar and nucleobase) in an oligonucleotide.

In certain embodiments, the oligonucleotides comprise or consist of a region having a gapmer nucleoside motif, which comprises two external regions or "wings" and a central or internal region or "gap." The three regions of a gapmer nucleoside motif (the 5'-wing, the gap, and the 3'-wing) form a contiguous sequence of nucleosides wherein at least some of the sugar moieties and/or nucleobases of the nucleosides of each of the wings differ from at least some of the sugar moieties and/or nucleobase of the nucleosides of the gap. Specifically, at least the nucleosides of each wing that are closest to the gap (the 3'-most nucleoside of the 5'-wing and the 5'-most nucleoside of the 3'-wing) differ from the neighboring gap nucleosides, thus defining the boundary between the wings and the gap. In certain embodiments, the nucleosides within the gap are the same as one another. In certain embodiments, the gap includes one or more nucleoside that differs from one or more other nucleosides of the gap. In certain embodiments, the nucleoside motifs of the two wings are the same as one another (symmetric gapmer). In certain embodiments, the nucleoside motifs of the 5'-wing differs from the nucleoside motif of the 3'-wing (asymmetric gapmer).

d. Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the invention provides oligomeric compounds which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a gapmer oligonucleotide has any of the above lengths.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range.

e. Certain Oligonucleotides

In certain embodiments, oligonucleotides of the present invention are characterized by their modification motif and overall length. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. One of skill in the art will appreciate that such motifs may be combined to create a variety of oligonucleotides. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

1. Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim Biophys. Acta, 1995, 1264, 229-

237), or an octadecylamine or hexylamino-carbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3' end of an oligomeric compound, but before one or more terminal group nucleosides. In certain embodiments, conjugate groups are placed within a terminal group. In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the motifs discussed above. Thus, for example, an oligomeric compound comprising an oligonucleotide having region of alternating nucleosides may comprise a terminal group.

B. Antisense Compounds

In certain embodiments, oligomeric compounds provided herein are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

a. Certain Antisense Activities and Mechanisms

In certain antisense activities, hybridization of an antisense compound results in recruitment of a protein that cleaves of the target nucleic acid. For example, certain antisense compounds result in RNase H mediated cleavage of target nucleic acid. RNase H is a cellular endonuclease that cleaves the RNA strand of an RNA:DNA duplex. The "DNA" in such an RNA:DNA duplex, need not be unmodified DNA. In certain embodiments, the invention provides antisense compounds that are sufficiently "DNA-like" to elicit RNase H activity. Such DNA-like antisense compounds include, but are not limited to gapmers having unmodified deoxyfuronose sugar moieties in the nucleosides of the gap and modified sugar moieties in the nucleosides of the wings.

Antisense activities may be observed directly or indirectly. In certain embodiments, observation or detection of an antisense activity involves observation or detection of a change in an amount of a target nucleic acid or protein encoded by such target nucleic acid; a change in the ratio of splice variants of a nucleic acid or protein; and/or a phenotypic change in a cell or animal.

In certain embodiments, compounds comprising oligonucleotides having a gapmer nucleoside motif described herein have desirable properties compared to non-gapmer oligonucleotides or to gapmers having other motifs. In certain circumstances, it is desirable to identify motifs resulting in a favorable combination of potent antisense activity and relatively low toxicity. In certain embodiments, compounds of the present invention have a favorable therapeutic index (measure of activity divided by measure of toxicity).

i. Mismatches to the Target Nucleic Acid

In certain embodiments, selective antisense compounds comprise one or more mismatched nucleobases relative to the target nucleic acid. In certain such embodiments, antisense activity against the target is reduced by such mismatch, but activity against the non-target is reduced by a greater amount. Thus, in certain embodiments selectivity is improved. Any nucleobase other than the differentiating nucleobase is suitable for a mismatch. In certain embodiments, however, the mismatch is specifically positioned within the gap of an oligonucleotide having a gapmer motif. In certain embodiments, a mismatch relative to the target nucleic acid is at positions 1, 2, 3, 4, 5, 6, 7, or 8 from the 5'-end of the gap region. In certain embodiments, a mismatch relative to the target nucleic acid is at positions 9, 8, 7, 6, 5, 4, 3, 2, 1 of the antisense compounds from the 3'-end of the gap region. In certain embodiments, a mismatch relative to the target nucleid acid is at positions 1, 2, 3, or 4 of the antisense compounds from the 5'-end of the wing region. In certain embodiments, a mismatch relative to the target nucleid acid is at positions 4, 3, 2, or 1 of the antisense compounds from the 3'-end of the wing region.

ii. Self Complementary Regions

In certain embodiments, selective antisense compounds comprise a region that is not complementary to the target. In certain embodiments, such region is complementary to another region of the antisense compound. Such regions are referred to herein as self-complementary regions. For example, in certain embodiments, an antisense compound has a first region at one end that is complementary to a second region at the other end. In certain embodiments, one of the first and second regions is complementary to the target nucleic acid. Unless the target nucleic acid also includes a self-complementary region, the other of the first and second region of the antisense compound will not be complementary to the target nucleic acid. For illustrative purposes, certain antisense compounds have the following nucleobase motif:

```
ABCXXXXXXXXXC'B'A';

ABCXXXXXXX(X/C')(X/B')(X/A');

(X/A)(X/B)(X/C)XXXXXXXXXC'B'A'
```

where each of A, B, and C are any nucleobase; A', B', and C' are the complementary bases to A, B, and C, respectively; each X is a nucleobase complementary to the target nucleic acid; and two letters in parentheses (e.g., (X/C')) indicates that the nucleobase is complementary to the target nucleic acid and to the designated nucleoside within the antisense oligonucleotide.

Without being bound to any mechanism, in certain embodiments, such antisense compounds are expected to form self-structure, which is disrupted upon contact with a target nucleic acid. Contact with a non-target nucleic acid is expected to disrupt the self-structure to a lesser degree, thus increasing selectivity compared to the same antisense compound lacking the self-complementary regions.

iii. Combinations of Features

Though it is clear to one of skill in the art, the above motifs and other elements for increasing selectivity may be used alone or in combination. For example, a single antisense compound may include any one, two, three, or more of: self-complementary regions, a mismatch relative to the target nucleic acid, a short nucleoside gap, an interrupted gap, and specific placement of the selective nucleoside.

C. Certain Target Nucleic Acids

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid is a non-coding RNA. In certain such embodiments, the target non-coding RNA is selected from: a long-non-coding RNA, a short non-coding RNA, an intronic RNA molecule, a snoRNA, a scaRNA, a microRNA (including pre-microRNA and mature microRNA), a ribosomal RNA, and promoter directed RNA. In certain embodiments, the target nucleic acid encodes a protein. In certain such embodiments, the target nucleic acid is selected from: an mRNA and a pre-mRNA, including intronic, exonic and untranslated regions. In certain embodiments, oligomeric compounds are at least partially complementary to more than one target nucleic acid. For example, antisense compounds of the present invention may mimic microRNAs, which typically bind to multiple targets.

In certain embodiments, the target nucleic acid is a nucleic acid other than a mature mRNA. In certain embodiments, the target nucleic acid is a nucleic acid other than a mature mRNA or a microRNA. In certain embodiments, the target nucleic acid is a non-coding RNA other than a microRNA. In certain embodiments, the target nucleic acid is a non-coding RNA other than a microRNA or an intronic region of a pre-mRNA. In certain embodiments, the target nucleic acid is a long non-coding RNA. In certain embodiments, the target RNA is an mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron. In certain embodiments, the target nucleic acid is selected from among non-coding RNA, including exonic regions of pre-mRNA. In certain embodiments, the target nucleic acid is a ribosomal RNA (rRNA).

In certain embodiments, the target nucleic acid is a non-coding RNA associated with splicing of other pre-mRNAs. In certain embodiments, the target nucleic acid is a nuclear-retained non-coding RNA. In certain embodiments, antisense compounds described herein are complementary to a target nucleic acid comprising a single-nucleotide polymorphism. In certain such embodiments, the antisense compound is capable of modulating expression of one allele of the single-nucleotide polymorphism-containing-target nucleic acid to a greater or lesser extent than it modulates another allele. In certain embodiments an antisense compound hybridizes to a single-nucleotide polymorphism-containing-target nucleic acid at the single-nucleotide polymorphism site.

a. Cartilage Oligomeric Matrix Protein (COMP)

In certain embodiments, antisense compounds comprise or consist of an oligonucleotide comprising a region that is complementary to a target nucleic acid, wherein the target nucleic acid is COMP. In certain embodiments, COMP nucleic acid has the sequence set forth in GENBANK Accession No. NM_000095.2 (incorporated herein as SEQ ID NO: 1). In certain embodiments, COMP encodes cartilage oligomeric matrix protein. Cartilage oligomeric matrix protein is a non-collagenous extracellular matrix protein expressed in cartilage, ligament, and tendon. Mutations in the COMP gene cause the skeletal dysplasias pseudoachondroplasia and multiple epiphyseal dysplasia. See, for example, Posey, K L: "*The role of cartilage oligomeric matrix protein* (*COMP*) *in skeletal disease*," Curr. Drug Targets. 2008 October; 9(10):869-77, which is hereby incorporated by reference in its entirety.

Pseudoachondroplasia is an inhereited bone growth disorder. Individuals having pseudoachondroplasia generally have a short stature with the average height of both males and females under 48 inches. Additionally, individuals with pseudoachondroplasia experience joint pain in adolescence that progresses to osteoarthritis in adulthood.

Multiple epiphyseal dysplasia affects the epiphyses, the ends of the long bones in the arms and legs. Symptoms of multiple epiphyseal dysplasia include joint pain, early-onset arthritis, and in some cases mild short stature and/or a waddling walk. Both dysplasias pseudoachondroplasia and multiple epiphyseal dysplasia stem from the intracellular retention of cartilage oligomeric matrix protein in the enlarged rough endoplasmic reticulum.

In certain embodiments, the retention of cartilage oligomeric matrix protein causes chondrocyte cell death which decreases linear bone growth. In certain embodiments, the retention of cartilage oligomeric matrix protein also reduces the stability of the extracellular matrix, which causes abnormalities in the extracellular matrix and makes the extracellular matrix erode during normal physical activity. In certain embodiments, increased serum cartilage levels of cartilage oligomeric matrix protein are found in patients with aggressive arthritis.

In certain embodiments, contacting a cell with an antisense compound complementary to COMP reduces the amount of cartilage oligomeric matrix protein. In certain embodiments, contacting a cell with an antisense compound complementary to COMP reduces the amount of cartilage oligomeric matrix protein and ameliorates one or more symptoms of pseudoachondroplasia. For example, in certain embodiments, contacting a cell with an antisense compound complementary to COMP reduces the amount of cartilage oligomeric matrix protein and ameliorates joint pain. For example, in certain embodments, contacting a cell with an antisense compound complementary to COMP reduces the amount of cartilage oligomeric matrix protein and ameliorates osteoarthritis. In certain embodments, contacting a cell with an antisense compound complementary to COMP reduces the amount of cartilage oligomeric matrix protein and dealys the onset of osteoarthritis. In certain embodments, contacting a cell with an antisense compound complementary to COMP reduces the amount of cartilage oligomeric matrix protein and slows the progression of osteoarthritis in subjects with pseudoachondroplasia.

In certain embodiments, contacting a cell with an antisense compound complementary to COMP reduces the amount of cartilage oligomeric matrix protein and ameliorates one or more symptoms of multiple epiphyseal dysplasia. For example, in certain embodments, contacting a cell with an antisense compound complementary to COMP reduces the amount of cartilage oligomeric matrix protein and ameliorates joint pain in subjects with multiple epiphyseal dysplasia. For example, in certain embodments, contacting a cell with an antisense compound complementary to COMP reduces the amount of cartilage oligomeric matrix protein and ameliorates osteoarthritis in subjects with multiple epiphyseal dysplasia. In certain embodments, contacting a cell with an antisense compound complementary to COMP reduces the amount of cartilage oligomeric matrix protein and dealys the onset of osteoarthritis in subjects with multiple epiphyseal dysplasia. In certain embodments, contacting a cell with an antisense compound complementary to COMP reduces the amount of cartilage oligomeric matrix protein and slow the progression of osteoarthritis in subjects with multiple epiphyseal dysplasia.

b. Certain Target Nucleic Acids in Certain Tissues

In certain embodiments, antisense compounds comprise or consist of an oligonucleotide comprising a region that is complementary to a target nucleic acid, wherein the target nucleic acid is expressed in the growth plate. In certain embodiments, antisense compounds comprise or consist of an oligonucleotide comprising a region that is complementary to a target nucleic acid, wherein the target nucleic acid is expressed in a tendon. In certain embodiments, antisense compounds comprise or consist of an oligonucleotide comprising a region that is complementary to a target nucleic acid, wherein the target nucleic acid is expressed in cartilage. In certain embodiments, the present disclosure provides antisense compounds capable of reducing target RNA in the growth plate, tendon, or cartilage. In certain embodiments, the present disclosure provides antisense compounds capable of reducing COMP in the growth plate, tendon, or cartilage.

D. Certain Pharmaceutical Compositions

In certain embodiments, the present invention provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration. In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain.

E. Administration

In certain embodiments, the compounds and compositions as described herein are administered parenterally.

In certain embodiments, parenteral administration is by infusion. Infusion can be chronic or continuous or short or intermittent. In certain embodiments, infused pharmaceutical agents are delivered with a pump. In certain embodiments, parenteral administration is by injection.

In certain embodiments, compounds and compositions are delivered to the CNS. In certain embodiments, compounds and compositions are delivered to the cerebrospinal fluid. In certain embodiments, compounds and compositions are administered to the brain parenchyma. In certain embodiments, compounds and compositions are delivered to an animal by intrathecal administration, or intracerebroventricular administration. Broad distribution of compounds and compositions, described herein, within the central nervous system may be achieved with intraparenchymal administration, intrathecal administration, or intracerebroventricular administration.

In certain embodiments, parenteral administration is by injection. The injection may be delivered with a syringe or a pump. In certain embodiments, the injection is a bolus injection. In certain embodiments, the injection is administered directly to a tissue, such as striatum, caudate, cortex, hippocampus and cerebellum.

Therefore, in certain embodiments, delivery of a compound or composition described herein can affect the pharmacokinetic profile of the compound or composition. In certain embodiments, injection of a compound or composition described herein, to a targeted tissue improves the pharmacokinetic profile of the compound or composition as compared to infusion of the compound or composition. In a certain embodiment, the injection of a compound or composition improves potency compared to broad diffusion, requiring less of the compound or composition to achieve similar pharmacology. In certain embodiments, similar pharmacology refers to the amount of time that a target mRNA and/or target protein is down-regulated (e.g. duration of action). In certain embodiments, methods of specifically localizing a pharmaceutical agent, such as by bolus injection, decreases median effective concentration (EC50) by a factor of about 50 (e.g. 50 fold less concentration in tissue is required to achieve the same or similar pharmacodynamic effect). In certain embodiments, methods of specifically localizing a pharmaceutical agent, such as by bolus injection, decreases median effective concentration (EC50) by a factor of 20, 25, 30, 35, 40, 45 or 50. In certain embodiments the pharmaceutical agent in an antisense compound as further described herein. In certain enbodiments, the targeted tissue is brain tissue. In certain embodiments the targeted tissue is striatal tissue. In certain embodiments, decreasing EC50 is desirable because it reduces the dose required to achieve a pharmacological result in a patient in need thereof.

In certain embodiments, an antisense oligonucleotide is delivered by injection or infusion once every month, every two months, every 90 days, every 3 months, every 6 months, twice a year or once a year.

F. Certain Combination Therapies

In certain embodiments, one or more pharmaceutical compositions are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions as described herein. In certain embodiments, one or more pharmaceutical compositions are co-administered with another pharmaceutical agent to treat an undesired effect of that other pharmaceutical agent. In certain embodiments, one or more pharmaceutical compositions are co-administered with another pharmaceutical agent to produce a combinational effect. In certain embodiments, one or more pharmaceutical compositions are co-administered with another pharmaceutical agent to produce a synergistic effect.

In certain embodiments, one or more pharmaceutical compositions and one or more other pharmaceutical agents are administered at the same time. In certain embodiments, one or more pharmaceutical compositions and one or more other pharmaceutical agents are administered at different times. In certain embodiments, one or more pharmaceutical compositions and one or more other pharmaceutical agents are prepared together in a single formulation. In certain embodiments, one or more pharmaceutical compositions and one or more other pharmaceutical agents are prepared separately.

In certain embodiments, pharmaceutical agents that may be co-administered with a pharmaceutical composition include antipsychotic agents, such as, e.g., haloperidol, chlorpromazine, clozapine, quetapine, and olanzapine; antidepressant agents, such as, e.g., fluoxetine, sertraline hydrochloride, venlafaxine and nortriptyline; tranquilizing agents such as, e.g., benzodiazepines, clonazepam, paroxetine, venlafaxin, and beta-blockers; mood-stabilizing agents such as, e.g., lithium, valproate, lamotrigine, and carbamazepine; paralytic agents such as, e.g., Botulinum toxin; and/or other experimental agents including, but not limited to, tetrabenazine (Xenazine), creatine, conezyme Q10, trehalose, docosahexanoic acids, ACR16, ethyl-EPA, atomoxetine, citalopram, dimebon, memantine, sodium phenylbutyrate, ramelteon, ursodiol, zyprexa, xenasine, tiapride, riluzole, amantadine, [1231]MNI-420, atomoxetine, tetrabenazine, digoxin, detromethorphan, warfarin, alprozam, ketoconazole, omeprazole, and minocycline. In certain embodiments, pharmaceutical agents, compounds, or compositions that may be co-administered with, before, or after a pharmaceutical composition comprising a modified oligonucleotide targeting COMP include anti-inflammatory and/or antioxidant agents, such as, e.g., Aspirin, turmeric, Resveratrol, grape seed extract, grapefruit seed extract, CoenzymeQ10, Liqsorb, Vitamine E, cucurmin, fish oil, omega-3 fatty acids, Fucoidan, Indometacin or Indomethacin, Ibuprofen, Naproxen, Lovaza, Cordycepin, and Diacerein.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "AT$^{me}$CGAUCG," wherein $^{me}$C indicates a cytosine base comprising a methyl group at the 5-position.

EXAMPLES

The following examples illustrate certain embodiments of the present invention and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif And, for example, where a particular high-affinity modification appears at a particular position, other high-affinity modifications at the same position are considered suitable, unless otherwise indicated.

Example 1: Antisense Inhibition of Human COMP by Antisense Oligonucleotides

A series of antisense oligonucleotides was designed to target different regions of human cartilage oligomeric matrix protein (COMP). The antisense oligonucleotides are targeted to the human mRNA SEQ ID NO: 1 (GENBANK Accession No. NM_000095.2).

The compounds were analyzed for their effects on gene target mRNA levels. HepG2 cells were plated at a density of 20,000 cells per well in 96 well plates and were transfected using electroporation with 2,000 nM compound or with no compound for untreated controls. After approximately 24 hours, RNA was isolated from the cells and COMP transcript levels were measured by quantitative real-time PCR using primer probe set RTS4252 (forward: 5'-CGCAGATGCT-TCGGGAACT-3', SEQ ID NO: 2; reverse: 5'-CACTCCAT-CACCGTGTTTTTCA-3', SEQ ID NO: 3; probe: 5'-AAAC-CAACGCGGCGCTGCA-3', SEQ ID NO: 4). COMP mRNA transcript levels were adjusted according to total RNA content, as measured by RIBOGREEN®. Results are presented in Tables 1-4 as average COMP mRNA expression level relative to untreated control cells. ISIS No. 644888 was tested in all four experiments and appears in all four tables as a reference.

The antisense oligonucleotides in Table 1-4 below are gapmers, composed of a central “gap” region consisting of 10 2'-deoxynucleotides, which is flanked on both sides (5' and 3') by three-nucleotide “wings”. The wings are composed of 4'-CH($CH_3$)—O-2' modified nucleotides, also known as constrained ethyl or cEt nucleotides. The internucleoside (backbone) linkages are phosphorothioate linkages. All cytosine residues are 5-methylcytosines. This example demonstrates that antisense oligonucleotides targeting human COMP inhibit expression of human COMP mRNA.

TABLE 1

Antisense oligonucleotides targeting human COMP

| ISIS No. | Sequence 5' to 3' | Start site on SEQ ID NO: 1 | Stop site on SEQ ID NO: 1 | COMP mRNA level (% control) | SEQ ID NO. |
|---|---|---|---|---|---|
| 644805 | CGCAGGCGGTGTCGGG | 43 | 58 | 66.7 | 5 |
| 644806 | GCAGAAGAACGCAGGC | 52 | 67 | 70.2 | 6 |
| 644807 | GCGCCGAGGGCAGCCA | 74 | 89 | 89.7 | 7 |
| 644808 | CCCTGTCCGGACGCGC | 86 | 101 | 146.9 | 8 |
| 644809 | AACGGGCTCTGGCCCT | 98 | 113 | 134.7 | 9 |
| 644810 | AGGTCTGAGCCCAACG | 110 | 125 | 143.3 | 10 |
| 644816 | TGACTGCTGCATCCCG | 252 | 267 | 78.8 | 11 |
| 644817 | CGCTGGGTAGGCCGGT | 274 | 289 | 68.1 | 12 |
| 644818 | GGGCGCGCAGTGGAGC | 300 | 315 | 75.9 | 13 |
| 644819 | GAAGCAGAAGCCGGGC | 312 | 327 | 70.6 | 14 |
| 644820 | GTCTGGATGCAGGCCA | 335 | 350 | 79.8 | 15 |
| 644821 | CCGCTCTCCGTCTGGA | 344 | 359 | 107 | 16 |
| 644822 | CCGCAGCGCGCGCCGC | 356 | 371 | 57.4 | 17 |
| 644823 | AGCCGTTGCCCGTGAA | 388 | 403 | 75.9 | 18 |
| 644824 | GTCGGTGCAGTGCGAG | 402 | 417 | 90.4 | 19 |
| 644825 | GGCAAGCCTCGCAGCG | 484 | 499 | 62.6 | 20 |
| 644826 | CCGCTGTACCCCGGCG | 500 | 515 | 99.7 | 21 |
| 644827 | CCACGCCCTGGTGGGT | 520 | 535 | 109.2 | 22 |
| 644828 | TTGGCGAAAGCCAGCC | 536 | 551 | 103.2 | 23 |
| 644829 | GTTGATGTCCGTGCAA | 567 | 582 | 46.2 | 24 |
| 644830 | GTTATGTTGCCCGGTC | 591 | 606 | 62.3 | 25 |

TABLE 1-continued

Antisense oligonucleotides targeting human COMP

| ISIS No. | Sequence 5' to 3' | Start site on SEQ ID NO: 1 | Stop site on SEQ ID NO: 1 | COMP mRNA level (% control) | SEQ ID NO. |
|---|---|---|---|---|---|
| 644831 | TGATGCACACGGAGTT | 616 | 631 | 89.3 | 26 |
| 644832 | TGGAAGGAGCCCCGGG | 635 | 650 | 75.6 | 27 |
| 644833 | GGCTGGCACGGGCCGC | 653 | 668 | 88.3 | 28 |
| 644834 | TGGTCGCCCACGAAGC | 671 | 686 | 80.6 | 29 |
| 644835 | CGCGCCGCTGGCAGCC | 694 | 709 | 86.5 | 30 |
| 644836 | TCGCTGGGCGAGCCGT | 728 | 743 | 72.1 | 31 |
| 644837 | TCTAGGACGCAGTCTG | 758 | 773 | 46.2 | 32 |
| 644838 | GAGCCATCGCGCTCTA | 770 | 785 | 118.2 | 33 |
| 644839 | ACGCACGACCGCGAGC | 782 | 797 | 71.4 | 34 |
| 644840 | GAGGATCCCGTTGCCG | 816 | 831 | 60.1 | 35 |
| 644841 | TGTCGCGACCACAGAG | 829 | 844 | 60.8 | 36 |
| 644842 | GAAGCCGTCTAGGTCA | 846 | 861 | 69.8 | 37 |
| 644843 | GCGCTCCGGGCAGCGC | 876 | 891 | 90.6 | 38 |
| 644844 | GTCACGCAGTTGTCCT | 902 | 917 | 35.8 | 39 |
| 644845 | GAGTTGGGCACAGTCA | 914 | 929 | 64.7 | 40 |
| 644846 | CCCGTCGGCATCCGGA | 975 | 990 | 93.1 | 41 |
| 644847 | GTCTGGGTTCCGCACC | 1026 | 1041 | 67.7 | 42 |
| 644848 | GCCCCACTTGTCCTCG | 1056 | 1071 | 67.9 | 43 |
| 644849 | GGGACCGGCAGTTGTC | 1081 | 1096 | 94.2 | 44 |
| 644850 | TCGTCGTTCTTCTGGG | 1094 | 1109 | 40.5 | 45 |
| 644851 | CCCCGGCCGTCCTGGT | 1124 | 1139 | 66.7 | 46 |
| 644852 | GGATCCGGTCGCCGTC | 1162 | 1177 | 99.3 | 47 |
| 644853 | CGGCCTGGTTGCGGAT | 1174 | 1189 | 73.3 | 48 |
| 644854 | CTGAGTTGGGTACCCT | 1201 | 1216 | 50.8 | 49 |
| 644855 | CGGGTTGCTCTTCTGG | 1269 | 1284 | 62.1 | 50 |
| 644856 | CATCCGCCTGATCCGG | 1282 | 1297 | 52.4 | 51 |
| 644857 | GCTGTCACAAGCATCT | 1317 | 1332 | 67.7 | 52 |
| 644858 | GGTCTTGATCGCTGTC | 1327 | 1342 | 41.5 | 53 |
| 644859 | CTCCATCCTGGTCTTG | 1336 | 1351 | 90.9 | 54 |
| 644860 | GTCCCGAGAGTCCTGA | 1359 | 1374 | 80.8 | 55 |
| 644861 | GGGCACTGTTAGGCAC | 1387 | 1402 | 82.4 | 56 |
| 644862 | CTCCTGGGCACTGTTA | 1392 | 1407 | 55.7 | 57 |
| 644863 | GACTGTCAGGGACTCC | 1462 | 1477 | 69.8 | 58 |
| 644864 | GTTAGGCACCAGGCGG | 1488 | 1503 | 63 | 59 |
| 644865 | CGCCCACGCCGTCCCT | 1525 | 1540 | 81.8 | 60 |
| 644866 | TTGTCTACCACCTTGT | 1568 | 1583 | 45 | 61 |

TABLE 1-continued

Antisense oligonucleotides targeting human COMP

| ISIS No. | Sequence 5' to 3' | Start site on SEQ ID NO: 1 | Stop site on SEQ ID NO: 1 | COMP mRNA level (% con-trol) | SEQ ID NO. |
|---|---|---|---|---|---|
| 644867 | CACGATCTCCCTTCCC | 1704 | 1719 | 50 | 62 |
| 644868 | CGTTTGCTCCATCTGC | 1881 | 1896 | 72.5 | 63 |
| 644869 | AGGCTCGGCCACAGCA | 1920 | 1935 | 57 | 64 |
| 644870 | GAGTTGGATGCCAGGC | 1932 | 1947 | 56.8 | 65 |
| 644871 | CTCTGTGTCTCCTGTA | 2004 | 2019 | 79 | 66 |
| 644872 | GCCGCACCTGGGACTC | 2017 | 2032 | 84 | 67 |
| 644873 | CCAACGATAGGACTTC | 2073 | 2088 | 58 | 68 |
| 644874 | CTGTCGGCCACCAGCT | 2147 | 2162 | 73.4 | 69 |
| 644875 | CCCAGGCGGCCACCCC | 2189 | 2204 | 81.2 | 70 |
| 644876 | CGCAGGTTGGCCCAGA | 2234 | 2249 | 86.7 | 71 |
| 644877 | TTGCAGCGGTAACGCA | 2246 | 2261 | 63.7 | 72 |
| 644880 | ATGGGTCTCATAGTCC | 2277 | 2292 | 53.7 | 73 |
| 644882 | TTGCCGCAGCTGATGG | 2289 | 2304 | 79.1 | 74 |
| 644884 | GGTCCCTAGGCTTGCC | 2300 | 2315 | 70.1 | 75 |
| 644886 | GGCGGGTCCTCACCCT | 2316 | 2331 | 21.7 | 76 |
| 644888 | GTCCTTCTGGTCTGAG | 1212 | 1227 | 49.4 | 77 |

TABLE 2

Antisense oligonucleotides targeting human COMP

| ISIS No. | Sequence 5' to 3' | Start site on SEQ ID NO: 1 | Stop site on SEQ ID NO: 1 | COMP mRNA level (% con-trol) | SEQ ID NO. |
|---|---|---|---|---|---|
| 644878 | ACGCAGGCGGTGTCGG | 44 | 59 | 82.5 | 78 |
| 644879 | TGAGCAGAAGAACGCA | 55 | 70 | 68.2 | 79 |
| 644881 | GACGCGCCGAGGGCAG | 77 | 92 | 109.3 | 80 |
| 644883 | TGGCCCTGTCCGGACG | 89 | 104 | 154.2 | 81 |
| 644885 | CCCAACGGGCTCTGGC | 101 | 116 | 122.4 | 82 |
| 644888 | GTCCTTCTGGTCTGAG | 1212 | 1227 | 63 | 77 |
| 644894 | TACTGACTGCTGCATC | 255 | 270 | 69.9 | 83 |
| 644895 | GCACGCTGGGTAGGCC | 277 | 292 | 109.3 | 84 |
| 644896 | GCCGGGCGCGCAGTGG | 303 | 318 | 68.3 | 85 |
| 644897 | GGGAAGCAGAAGCCGG | 314 | 329 | 68.1 | 86 |
| 644898 | TCCGTCTGGATGCAGG | 338 | 353 | 71 | 87 |
| 644899 | GCGCCGCTCTCCGTCT | 347 | 362 | 88.2 | 88 |
| 644900 | GGGCCGCAGCGCGCGC | 359 | 374 | 86.1 | 89 |

TABLE 2-continued

Antisense oligonucleotides targeting human COMP

| ISIS No. | Sequence 5' to 3' | Start site on SEQ ID NO: 1 | Stop site on SEQ ID NO: 1 | COMP mRNA level (% con-trol) | SEQ ID NO. |
|---|---|---|---|---|---|
| 644901 | GCGAGCCGTTGCCCGT | 391 | 406 | 107.1 | 90 |
| 644902 | CGTCGGTGCAGTGCGA | 403 | 418 | 115.9 | 91 |
| 644903 | CGGCGGGCAAGCCTCG | 489 | 504 | 89.4 | 92 |
| 644904 | GGGCCGCTGTACCCCG | 503 | 518 | 91.1 | 93 |
| 644905 | GCCCCACGCCCTGGTG | 523 | 538 | 109.7 | 94 |
| 644906 | GCCTTGGCGAAAGCCA | 539 | 554 | 77 | 95 |
| 644907 | CCCGGTCTCACACTCG | 582 | 597 | 63.5 | 96 |
| 644908 | GCAGTTATGTTGCCCG | 594 | 609 | 51.2 | 97 |
| 644909 | CCCCGGGTGTTGATGC | 626 | 641 | 76.4 | 98 |
| 644910 | CACTGGAAGGAGCCCC | 638 | 653 | 79 | 99 |
| 644911 | ACGAAGCCGGGCTGGC | 662 | 677 | 92.4 | 100 |
| 644912 | GCCTGGTCGCCCACGA | 674 | 689 | 74.1 | 101 |
| 644913 | GTGCGCGCCGCTGGCA | 697 | 712 | 83 | 102 |
| 644914 | GCACTCGCTGGGCGAG | 732 | 747 | 102.8 | 103 |
| 644915 | CGCTCTAGGACGCAGT | 761 | 776 | 102.9 | 104 |
| 644916 | CGCGAGCCATCGCGCT | 773 | 788 | 103.5 | 105 |
| 644917 | ACACACGCACGACCGC | 786 | 801 | 89.8 | 106 |
| 644918 | ACAGAGGATCCCGTTG | 819 | 834 | 97.2 | 107 |
| 644919 | CAGTGTCGCGACCACA | 832 | 847 | 73.6 | 108 |
| 644920 | GCAGCGCAGCTTCTCG | 867 | 882 | 95.8 | 109 |
| 644921 | CTTACGGCACTGGCGC | 888 | 903 | 54.9 | 110 |
| 644922 | ACAGTCACGCAGTTGT | 905 | 920 | 74.4 | 111 |
| 644923 | ATCCGGATCGCAGGCG | 966 | 981 | 75.1 | 112 |
| 644924 | CCCCGTCCCCGTCGGC | 982 | 997 | 85.5 | 113 |
| 644925 | TTGCGCTGGTCTGGGT | 1034 | 1049 | 78.3 | 114 |
| 644926 | ATCGCCCCACTTGTCC | 1059 | 1074 | 78.9 | 115 |
| 644927 | TGGGACCGGCAGTTGT | 1082 | 1097 | 87.1 | 116 |
| 644928 | TTGGTCGTCGTTCTTC | 1098 | 1113 | 61.4 | 117 |
| 644929 | CGCCCCGGCCGTCCTG | 1126 | 1141 | 75.7 | 118 |
| 644930 | TGCGGATCCGGTCGCC | 1165 | 1180 | 88.5 | 119 |
| 644931 | CAGTTGTCGGCCTGGT | 1181 | 1196 | 50.9 | 120 |
| 644932 | TACCATCGCCATCACT | 1228 | 1243 | 69.9 | 121 |
| 644933 | ATCCGGGTTGCTCTTC | 1272 | 1287 | 73.5 | 122 |
| 644934 | CACATCCGCCTGATCC | 1284 | 1299 | 44.9 | 123 |
| 644935 | CGCTGTCACAAGCATC | 1318 | 1333 | 52.8 | 124 |
| 644936 | TGGTCTTGATCGCTGT | 1328 | 1343 | 49.2 | 125 |

TABLE 2-continued

Antisense oligonucleotides targeting human COMP

| ISIS No. | Sequence 5' to 3' | Start site on SEQ ID NO: 1 | Stop site on SEQ ID NO: 1 | COMP mRNA level (% control) | SEQ ID NO. |
|---|---|---|---|---|---|
| 644937 | TCTCCATCCTGGTCTT | 1337 | 1352 | 82.4 | 126 |
| 644938 | AGTTGTCCCGAGAGTC | 1363 | 1378 | 70.6 | 127 |
| 644939 | CTGGGCACTGTTAGGC | 1389 | 1404 | 55.3 | 128 |
| 644940 | AGTCCTCCTGGGCACT | 1396 | 1411 | 57.2 | 129 |
| 644941 | CCCGACTGTCAGGGAC | 1465 | 1480 | 85.1 | 130 |
| 644942 | CGTCCTCCTGGCCGGG | 1504 | 1519 | 64.8 | 131 |
| 644943 | ACCTTGTCTGCATCAA | 1559 | 1574 | 39.8 | 132 |
| 644944 | ATCTTGTCTACCACCT | 1571 | 1586 | 50.6 | 133 |
| 644945 | CTGCACGATCTCCCTT | 1707 | 1722 | 66.8 | 134 |
| 644946 | TTCGCCTGCCAATACG | 1895 | 1910 | 60.1 | 135 |
| 644947 | GCCAGGCTCGGCCACA | 1923 | 1938 | 91.9 | 136 |
| 644948 | TGTGGAAGACTTCACA | 1953 | 1968 | 102.1 | 137 |
| 644949 | GGGACTCTGTGTCTCC | 2008 | 2023 | 98.6 | 138 |
| 644950 | TCGCGGGTCCTTCCAC | 2037 | 2052 | 71 | 139 |
| 644951 | GGCCCTCATAGAATCG | 2128 | 2143 | 93.6 | 140 |
| 644952 | TTGCTGTCGGCCACCA | 2150 | 2165 | 56.8 | 141 |
| 644953 | ACCCCCAGGCGGCCAC | 2192 | 2207 | 68.6 | 142 |
| 644954 | TAACGCAGGTTGGCCC | 2237 | 2252 | 112.6 | 143 |
| 644955 | ATTGCAGCGGTAACGC | 2247 | 2262 | 65.7 | 144 |
| 644956 | GCTGATGGGTCTCATA | 2281 | 2296 | 78.8 | 145 |
| 644957 | GCTTGCCGCAGCTGAT | 2291 | 2306 | 70.2 | 146 |
| 644958 | CACCCTGGTCCCTAGG | 2306 | 2321 | 83.9 | 147 |
| 644959 | TCCGGCGGGTCCTCAC | 2319 | 2334 | 15.8 | 148 |

TABLE 3

Antisense oligonucleotides targeting human COMP

| ISIS No. | Sequence 5' to 3' | Start site on SEQ ID NO: 1 | Stop site on SEQ ID NO: 1 | COMP mRNA level (% control) | SEQ ID NO. |
|---|---|---|---|---|---|
| 644888 | GTCCTTCTGGTCTGAG | 1212 | 1227 | 65.9 | 77 |
| 644960 | GAACGCAGGCGGTGTC | 46 | 61 | 55.5 | 149 |
| 644961 | GGGTGAGCAGAAGAAC | 58 | 73 | 94.6 | 150 |
| 644962 | CCGGACGCGCCGAGGG | 80 | 95 | 122.5 | 151 |
| 644963 | CTCTGGCCCTGTCCGG | 92 | 107 | 301.3 | 152 |
| 644964 | GAGCCCAACGGGCTCT | 104 | 119 | 102.4 | 153 |
| 644970 | CTGCATCCCGCACGCG | 246 | 261 | 63.5 | 154 |

TABLE 3-continued

Antisense oligonucleotides targeting human COMP

| ISIS No. | Sequence 5' to 3' | Start site on SEQ ID NO: 1 | Stop site on SEQ ID NO: 1 | COMP mRNA level (% control) | SEQ ID NO. |
|---|---|---|---|---|---|
| 644971 | CGTACTGACTGCTGCA | 257 | 272 | 65.3 | 155 |
| 644972 | GCCGCACGCTGGGTAG | 280 | 295 | 74.5 | 156 |
| 644973 | GAAGCCGGGCGCGCAG | 306 | 321 | 63 | 157 |
| 644974 | ATGCAGGCCACGCCGG | 329 | 344 | 64 | 158 |
| 644975 | CTCTCCGTCTGGATGC | 341 | 356 | 74.2 | 159 |
| 644976 | CGCGCGCCGCTCTCCG | 350 | 365 | 76.1 | 160 |
| 644977 | CCGTGAAGCCCGCGGG | 379 | 394 | 89 | 161 |
| 644978 | GCAGTGCGAGCCGTTG | 396 | 411 | 65.5 | 162 |
| 644979 | ATACAGCGGACTCGGG | 449 | 464 | 54.5 | 163 |
| 644980 | ACCCCGGCGGGCAAGC | 493 | 508 | 99.7 | 164 |
| 644981 | GGTGGGGCCGCTGTAC | 507 | 522 | 99.8 | 165 |
| 644982 | AAGCCAGCCCCACGCC | 529 | 544 | 117 | 166 |
| 644983 | TTGGCCTTGGCGAAAG | 542 | 557 | 54.1 | 167 |
| 644984 | TTGCCCGGTCTCACAC | 585 | 600 | 60 | 168 |
| 644985 | GACGCAGTTATGTTGC | 597 | 612 | 42.3 | 169 |
| 644986 | GAGCCCCGGGTGTTGA | 629 | 644 | 63.5 | 170 |
| 644987 | CCGCACTGGAAGGAGC | 641 | 656 | 69.5 | 171 |
| 644988 | CCCACGAAGCCGGGCT | 665 | 680 | 64.4 | 172 |
| 644989 | GCTGGCAGCCGGACGC | 688 | 703 | 72.7 | 173 |
| 644990 | GCTGTGCGCGCCGCTG | 700 | 715 | 92 | 174 |
| 644991 | GTGGCACTCGCTGGGC | 735 | 750 | 69.2 | 175 |
| 644992 | TCGCGCTCTAGGACGC | 764 | 779 | 120.3 | 176 |
| 644993 | GACCGCGAGCCATCGC | 776 | 791 | 90.5 | 177 |
| 644994 | GGCACACACGCACGAC | 789 | 804 | 46 | 178 |
| 644995 | GACCACAGAGGATCCC | 823 | 838 | 80.5 | 179 |
| 644996 | AGGTCAGTGTCGCGAC | 836 | 851 | 66.2 | 180 |
| 644997 | CGGGCAGCGCAGCTTC | 870 | 885 | 67.6 | 181 |
| 644998 | GTCCTTACGGCACTGG | 891 | 906 | 40.9 | 182 |
| 644999 | GGCACAGTCACGCAGT | 908 | 923 | 46.8 | 183 |
| 645000 | GGCATCCGGATCGCAG | 969 | 984 | 91.9 | 184 |
| 645001 | CCGCACCAGCGGGCAG | 1017 | 1032 | 81 | 185 |
| 645002 | GTGTTGCGCTGGTCTG | 1037 | 1052 | 42.6 | 186 |
| 645003 | CGCATCGCCCCACTTG | 1062 | 1077 | 31.2 | 187 |
| 645004 | TTCTGGGACCGGCAGT | 1085 | 1100 | 70.2 | 188 |
| 645005 | TGTGTCCTTTTGGTCG | 1107 | 1122 | 43.1 | 189 |
| 645006 | TCGCACGCATCGCCCC | 1067 | 1082 | 27.7 | 190 |

TABLE 3-continued

Antisense oligonucleotides targeting human COMP

| ISIS No. | Sequence 5' to 3' | Start site on SEQ ID NO: 1 | Stop site on SEQ ID NO: 1 | COMP mRNA level (% control) | SEQ ID NO. |
|---|---|---|---|---|---|
| 645007 | GGTTGCGGATCCGGTC | 1168 | 1183 | 75.4 | 191 |
| 645008 | AGGGCAGTTGTCGGCC | 1185 | 1200 | 74.3 | 192 |
| 645009 | CCTATACCATCGCCAT | 1232 | 1247 | 45.3 | 193 |
| 645010 | CCTGATCCGGGTTGCT | 1276 | 1291 | 34.6 | 194 |
| 645011 | AGCATCTCCCACAAAG | 1308 | 1323 | 56.3 | 195 |
| 645012 | TCGCTGTCACAAGCAT | 1319 | 1334 | 50.8 | 196 |
| 645013 | CCTGGTCTTGATCGCT | 1330 | 1345 | 58 | 197 |
| 645014 | AGAGTCCTGATGTCCG | 1353 | 1368 | 35.6 | 198 |
| 645015 | GTTAGGCACCGTGGGA | 1380 | 1395 | 43.9 | 199 |
| 645016 | CCTGGGCACTGTTAGG | 1390 | 1405 | 78.5 | 200 |
| 645017 | TGTCAGGGACTCCGTC | 1459 | 1474 | 46.8 | 201 |
| 645020 | TGTCCCGACTGTCAGG | 1468 | 1483 | 57.5 | 202 |
| 645022 | CGCCGTCCCTGTCCGC | 1519 | 1534 | 44.8 | 203 |
| 645024 | ACCACCTTGTCTGCAT | 1562 | 1577 | 54.1 | 204 |
| 645026 | TCGATCTTGTCTACCA | 1574 | 1589 | 44.7 | 205 |
| 645028 | AGTGTAACCCACAGCC | 1746 | 1761 | 88.4 | 206 |
| 645030 | GGGTTCGCCTGCCAAT | 1898 | 1913 | 51.1 | 207 |
| 645032 | GATGCCAGGCTCGGCC | 1926 | 1941 | 70.8 | 208 |
| 645034 | GCCTGTGGAAGACTTC | 1956 | 1971 | 46.6 | 209 |
| 645036 | CCTGGGACTCTGTGTC | 2011 | 2026 | 83.5 | 210 |
| 645038 | GTTTCGCGGGTCCTTC | 2040 | 2055 | 77.6 | 211 |
| 645040 | CAGGGCCCTCATAGAA | 2131 | 2146 | 97.4 | 212 |
| 645042 | TGTGTCCAAGACCACG | 2166 | 2181 | 63.5 | 213 |
| 645044 | GAAGACCCCCAGGCGG | 2196 | 2211 | 64.9 | 214 |
| 645046 | CGGTAACGCAGGTTGG | 2240 | 2255 | 34.7 | 215 |
| 645048 | CATAGTCCTCTGGGAT | 2269 | 2284 | 46.1 | 216 |
| 645050 | GCAGCTGATGGGTCTC | 2284 | 2299 | 69.2 | 217 |
| 645052 | TAGGCTTGCCGCAGCT | 2294 | 2309 | 67.1 | 218 |
| 645054 | CTCACCCTGGTCCCTA | 2308 | 2323 | 44.8 | 219 |
| 645056 | TCATCCGGCGGGTCCT | 2322 | 2337 | 10.3 | 220 |

TABLE 4

Antisense oligonucleotides targeting human COMP

| ISIS No. | Sequence 5' to 3' | Start site on SEQ ID NO: 1 | Stop site on SEQ ID NO: 1 | COMP mRNA level (% control) | SEQ ID NO. |
|---|---|---|---|---|---|
| 644888 | GTCCTTCTGGTCTGAG | 1212 | 1227 | 39.5 | 77 |
| 645018 | GAAGAACGCAGGCGGT | 49 | 64 | 65.2 | 221 |
| 645019 | GCCAGGGTGAGCAGAA | 62 | 77 | 136.2 | 222 |
| 645021 | TGTCCGGACGCGCCGA | 83 | 98 | 120.9 | 223 |
| 645023 | GGGCTCTGGCCCTGTC | 95 | 110 | 121 | 224 |
| 645025 | TCTGAGCCCAACGGGC | 107 | 122 | 133.3 | 225 |
| 645037 | CTGCTGCATCCCGCAC | 249 | 264 | 76.4 | 226 |
| 645039 | TGGGTAGGCCGGTGCG | 271 | 286 | 82.7 | 227 |
| 645041 | CGCGCAGTGGAGCAGG | 297 | 312 | 57.7 | 228 |
| 645043 | GCAGAAGCCGGGCGCG | 309 | 324 | 76.9 | 229 |
| 645045 | TGGATGCAGGCCACGC | 332 | 347 | 76.3 | 230 |
| 645047 | GCTCTCCGTCTGGATG | 342 | 357 | 89.7 | 231 |
| 645049 | CAGCGCGCGCCGCTCT | 353 | 368 | 87.2 | 232 |
| 645051 | TGCCCGTGAAGCCCGC | 382 | 397 | 86.3 | 233 |
| 645053 | GGTGCAGTGCGAGCCG | 399 | 414 | 105.7 | 234 |
| 645055 | TGATACAGCGGACTCG | 451 | 466 | 65.1 | 235 |
| 645057 | CTGTACCCCGGCGGGC | 497 | 512 | 74.3 | 236 |
| 645058 | CTGGTGGGTGGGGCCG | 513 | 528 | 118.5 | 237 |
| 645059 | GCGAAAGCCAGCCCCA | 533 | 548 | 106.3 | 238 |
| 645060 | GATGTCCGTGCAAACC | 564 | 579 | 49.8 | 239 |
| 645061 | ATGTTGCCCGGTCTCA | 588 | 603 | 86 | 240 |
| 645062 | TGCACACGGAGTTGGG | 613 | 628 | 90.4 | 241 |
| 645063 | AAGGAGCCCCGGGTGT | 632 | 647 | 86.8 | 242 |
| 645064 | TGGCACGGGCCGCACT | 650 | 665 | 65.5 | 243 |
| 645065 | TCGCCCACGAAGCCGG | 668 | 683 | 82.8 | 244 |
| 645066 | GCCGCTGGCAGCCGGA | 691 | 706 | 98.7 | 245 |
| 645067 | CTGGGCGAGCCGTCGG | 725 | 740 | 90.7 | 246 |
| 645068 | CGCAGTCTGCATGCTC | 751 | 766 | 73.2 | 247 |
| 645069 | CCATCGCGCTCTAGGA | 767 | 782 | 94.3 | 248 |
| 645070 | CACGACCGCGAGCCAT | 779 | 794 | 58.1 | 249 |
| 645071 | GATCCCGTTGCCGGCC | 813 | 828 | 111.6 | 250 |
| 645072 | CGCGACCACAGAGGAT | 826 | 841 | 64.3 | 251 |
| 645073 | TCTAGGTCAGTGTCGC | 839 | 854 | 68.3 | 252 |
| 645074 | CTCCGGGCAGCGCAGC | 873 | 888 | 96.6 | 253 |
| 645075 | GTTGTCCTTACGGCAC | 894 | 909 | 64.8 | 254 |
| 645076 | TTGGGCACAGTCACGC | 911 | 926 | 73.3 | 255 |

TABLE 4-continued

| Antisense oligonucleotides targeting human COMP | | | | | |
|---|---|---|---|---|---|
| ISIS No. | Sequence 5' to 3' | Start site on SEQ ID NO: 1 | Stop site on SEQ ID NO: 1 | COMP mRNA level (% control) | SEQ ID NO. |
| 645077 | GTCGGCATCCGGATCG | 972 | 987 | 58.7 | 256 |
| 645078 | GTTCCGCACCAGCGGG | 1020 | 1035 | 103.1 | 257 |
| 645079 | CGTCCGTGTTGCGCTG | 1042 | 1057 | 40.8 | 258 |
| 645080 | GCACGCATCGCCCCAC | 1065 | 1080 | 46.4 | 259 |
| 645081 | TTCTTCTGGGACCGGC | 1088 | 1103 | 87.4 | 260 |
| 645082 | TCTGTGTCCTTTTGGT | 1109 | 1124 | 61.6 | 261 |
| 645083 | TCCGGTCGCCGTCGAT | 1159 | 1174 | 84.6 | 262 |
| 645084 | CCTGGTTGCGGATCCG | 1171 | 1186 | 72.3 | 263 |
| 645085 | CCTAGGGCAGTTGTCG | 1188 | 1203 | 73.8 | 264 |
| 645086 | CCCCTATACCATCGCC | 1234 | 1249 | 64.1 | 265 |
| 645087 | CCGCCTGATCCGGGTT | 1279 | 1294 | 50.2 | 266 |
| 645088 | TCACAAGCATCTCCCA | 1313 | 1328 | 82 | 267 |
| 645089 | CTTGATCGCTGTCACA | 1324 | 1339 | 36.2 | 268 |
| 645090 | CATCCTGGTCTTGATC | 1333 | 1348 | 77 | 269 |
| 645091 | CCGAGAGTCCTGATGT | 1356 | 1371 | 90.4 | 270 |
| 645092 | ACTGTTAGGCACCGTG | 1383 | 1398 | 55.4 | 271 |
| 645093 | TCCTGGGCACTGTTAG | 1391 | 1406 | 54.4 | 272 |
| 645094 | CTGTCAGGGACTCCGT | 1460 | 1475 | 41.5 | 273 |
| 645095 | CGGCAGTTGTCCCGAC | 1475 | 1490 | 97.4 | 274 |
| 645096 | CCACGCCGTCCCTGTC | 1522 | 1537 | 74.8 | 275 |
| 645097 | TCTACCACCTTGTCTG | 1565 | 1580 | 68.6 | 276 |
| 645098 | CTCCGGGTCCAGCACG | 1647 | 1662 | 69.6 | 277 |
| 645099 | GGCAGTGTAACCCACA | 1749 | 1764 | 69.9 | 278 |
| 645100 | CTCGGCCACAGCACGG | 1917 | 1932 | 51.9 | 279 |
| 645101 | TTGGATGCCAGGCTCG | 1929 | 1944 | 121.3 | 280 |
| 645102 | CCGCAGCTGTTCCCCG | 1974 | 1989 | 66 | 281 |
| 645103 | GCACCTGGGACTCTGT | 2014 | 2029 | 85.5 | 282 |
| 645104 | ACGATAGGACTTCTTG | 2070 | 2085 | 50 | 283 |
| 645105 | GGCCACCAGCTCAGGG | 2142 | 2157 | 115.4 | 284 |
| 645106 | GGTTGTGTCCAAGACC | 2169 | 2184 | 69.6 | 285 |
| 645107 | GCAGAAGACCCCCAGG | 2199 | 2214 | 62.7 | 286 |
| 645108 | CAGCGGTAACGCAGGT | 2243 | 2258 | 67.5 | 287 |
| 645109 | GGTCTCATAGTCCTCT | 2274 | 2289 | 40.4 | 288 |
| 645110 | GCCGCAGCTGATGGGT | 2287 | 2302 | 72.3 | 289 |
| 645111 | CCCTAGGCTTGCCGCA | 2297 | 2312 | 56.6 | 290 |

TABLE 4-continued

| Antisense oligonucleotides targeting human COMP | | | | | |
|---|---|---|---|---|---|
| ISIS No. | Sequence 5' to 3' | Start site on SEQ ID NO: 1 | Stop site on SEQ ID NO: 1 | COMP mRNA level (% control) | SEQ ID NO. |
| 645112 | GGGTCCTCACCCTGGT | 2313 | 2328 | 57.3 | 291 |
| 645113 | CTGTCATCCGGCGGGT | 2325 | 2340 | 36 | 292 |

Example 2: Dose Dependent Antisense Inhibition of COMP in HepG2 Cells

Select compounds listed in Tables 1-4 were further evaluated for antisense inhibition of COMP in vitro. HepG2 cells were plated at a density of 20,000 cells per well in 96-well plates and were transfected via electroporation with concentrations of the oligonucleotides listed in Table 5 or with no oligonucleotide for untreated controls. After approximately 24 hours, RNA was isolated from the cells and COMP transcript levels were measured by quantitative real-time PCR using primer probe set RTS4252, and COMP mRNA expression was quantitated using qRT-PCR, as described in Example 1. The results presented in Table 5 are the average values relative to the untreated control cells. This example demonstrates that ISIS 644844, 644886, 644943, 644959, 645003, 645006, 645010, 645014, 645046, 645056, 645089, and 645113 inhibit COMP mRNA expression in HepG2 in a dose dependent manner.

TABLE 5

| Antisense inhibition of COMP in HepG2 cells | | |
|---|---|---|
| ISIS No. | Concentration (nM) | mRNA level (% Control) |
| 644844 | 37.0 | 94 |
| | 111 | 84 |
| | 333 | 44 |
| | 1000 | 26 |
| | 3000 | 22 |
| | 9000 | 4 |
| 644886 | 37.0 | 106 |
| | 111 | 88 |
| | 333 | 50 |
| | 1000 | 18 |
| | 3000 | 6 |
| | 9000 | 3 |
| 644943 | 37.0 | 96 |
| | 111 | 79 |
| | 333 | 50 |
| | 1000 | 24 |
| | 3000 | 8 |
| | 9000 | 4 |
| 644959 | 37.0 | 84 |
| | 111 | 57 |
| | 333 | 15 |
| | 1000 | 7 |
| | 3000 | 3 |
| | 9000 | 7 |
| 645003 | 37.0 | 84 |
| | 111 | 74 |
| | 333 | 35 |
| | 1000 | 19 |
| | 3000 | 8 |
| | 9000 | 5 |
| 645006 | 37.0 | 107 |
| | 111 | 82 |

TABLE 5-continued

| Antisense inhibition of COMP in HepG2 cells | | |
|---|---|---|
| ISIS No. | Concentration (nM) | mRNA level (% Control) |
| | 333 | 44 |
| | 1000 | 22 |
| | 3000 | 10 |
| | 9000 | 4 |
| 645010 | 37.0 | 108 |
| | 111 | 90 |
| | 333 | 58 |
| | 1000 | 29 |
| | 3000 | 18 |
| | 9000 | 9 |
| 645014 | 37.0 | 93 |
| | 111 | 73 |
| | 333 | 56 |
| | 1000 | 31 |
| | 3000 | 13 |
| | 9000 | 5 |
| 645046 | 37.0 | 98 |
| | 111 | 100 |
| | 333 | 92 |
| | 1000 | 44 |
| | 3000 | 13 |
| | 9000 | 6 |
| 645056 | 37.0 | 81 |
| | 111 | 54 |
| | 333 | 15 |
| | 1000 | 5 |
| | 3000 | 3 |
| | 9000 | 2 |
| 645089 | 37.0 | 101 |
| | 111 | 84 |
| | 333 | 69 |
| | 1000 | 45 |
| | 3000 | 15 |
| | 9000 | 8 |
| 645113 | 37.0 | 106 |
| | 111 | 81 |
| | 333 | 45 |
| | 1000 | 31 |
| | 3000 | 12 |
| | 9000 | 6 |

Example 3: Dose Dependent Antisense Inhibition of COMP in Human Tendon Cells

The compounds listed in Table 5 were further evaluated for antisense inhibition of COMP in tendon cells. Human tendon cells were plated at a density of 20,000 cells per well in 96-well plates and were transfected via electroporation with concentrations of the oligonucleotides listed in Table 6 or with no oligonucleotide for untreated controls. After approximately 24 hours, RNA was isolated from the cells and COMP transcript levels were measured by quantitative real-time PCR using primer probe set RTS4252, and COMP mRNA expression was quantitated using qRT-PCR, as described in Example 1. The results presented in Table 6 are the average values relative to the untreated control cells. These results demonstrate that antisense oligonucleotides targeting human COMP inhibit COMP mRNA expression in human tendon cells in a dose dependent manner.

TABLE 6

| Antisense inhibition of COMP in human tendon cells | | |
|---|---|---|
| ISIS No. | Concentration (nM) | mRNA level (% Control) |
| 644844 | 37.0 | 74 |
| | 111 | 72 |
| | 333 | 70 |
| | 1000 | 86 |
| | 3000 | 42 |
| | 9000 | 16 |
| 644886 | 37.0 | 64 |
| | 111 | 75 |
| | 333 | 80 |
| | 1000 | 67 |
| | 3000 | 58 |
| | 9000 | 40 |
| 644943 | 37.0 | 141 |
| | 111 | 86 |
| | 333 | 79 |
| | 1000 | 64 |
| | 3000 | 46 |
| | 9000 | 17 |
| 644959 | 37.0 | 75 |
| | 111 | 59 |
| | 333 | 46 |
| | 1000 | 22 |
| | 3000 | 11 |
| | 9000 | 4 |
| 645003 | 37.0 | 77 |
| | 111 | 62 |
| | 333 | 70 |
| | 1000 | 59 |
| | 3000 | 60 |
| | 9000 | 41 |
| 645006 | 37.0 | 90 |
| | 111 | 128 |
| | 333 | 95 |
| | 1000 | 80 |
| | 3000 | 49 |
| | 9000 | 19 |
| 645010 | 37.0 | 133 |
| | 111 | 64 |
| | 333 | 82 |
| | 1000 | 54 |
| | 3000 | 45 |
| | 9000 | 33 |
| 645014 | 37.0 | 98 |
| | 111 | 67 |
| | 333 | 90 |
| | 1000 | 72 |
| | 3000 | 55 |
| | 9000 | 46 |
| 645046 | 37.0 | 80 |
| | 111 | 53 |
| | 333 | 53 |
| | 1000 | 66 |
| | 3000 | 28 |
| | 9000 | 8 |
| 645056 | 37.0 | 91 |
| | 111 | 92 |
| | 333 | 46 |
| | 1000 | 13 |
| | 3000 | 10 |
| | 9000 | 3 |
| 645089 | 37.0 | 126 |
| | 111 | 93 |
| | 333 | 130 |
| | 1000 | 75 |
| | 3000 | 45 |
| | 9000 | 19 |
| 645113 | 37.0 | 84 |
| | 111 | 76 |
| | 333 | 106 |
| | 1000 | 40 |
| | 3000 | 38 |
| | 9000 | 9 |

Example 4: Dose Dependent Antisense Inhibition of COMP in Human Tendon Cells

Additional compounds selected from Tables 1-4 were evaluated for antisense inhibition of COMP in tendon cells.

The procedure is described in Example 3. The results presented in Tables 7-9 are the average values relative to the untreated control cells. These results demonstrate that antisense oligonucleotides targeting human COMP inhibit COMP mRNA expression in human tendon cells in a dose dependent manner.

TABLE 7

Antisense inhibition of COMP in human tendon cells

| ISIS No. | Concentration (nM) | mRNA level (% Control) |
|---|---|---|
| 644888 | 333 | 63 |
| | 1000 | 44 |
| | 3000 | 16 |
| | 9000 | 12 |
| 644959 | 333 | 105 |
| | 1000 | 51 |
| | 3000 | 46 |
| | 9000 | 49 |
| 644994 | 333 | 69 |
| | 1000 | 68 |
| | 3000 | 57 |
| | 9000 | 37 |
| 644999 | 333 | 82 |
| | 1000 | 57 |
| | 3000 | 43 |
| | 9000 | 14 |
| 645009 | 333 | 65 |
| | 1000 | 41 |
| | 3000 | 22 |
| | 9000 | 10 |
| 645017 | 333 | 80 |
| | 1000 | 60 |
| | 3000 | 40 |
| | 9000 | 26 |
| 645022 | 333 | 66 |
| | 1000 | 43 |
| | 3000 | 27 |
| | 9000 | 16 |
| 645034 | 333 | 74 |
| | 1000 | 50 |
| | 3000 | 39 |
| | 9000 | 18 |
| 645048 | 333 | 74 |
| | 1000 | 54 |
| | 3000 | 31 |
| | 9000 | 13 |
| 645054 | 333 | 54 |
| | 1000 | 40 |
| | 3000 | 20 |
| | 9000 | 6 |
| 645060 | 333 | 59 |
| | 1000 | 45 |
| | 3000 | 29 |
| | 9000 | 18 |
| 645079 | 333 | 81 |
| | 1000 | 43 |
| | 3000 | 29 |
| | 9000 | 9 |
| 645080 | 333 | 66 |
| | 1000 | 57 |
| | 3000 | 22 |
| | 9000 | 13 |
| 645087 | 333 | 97 |
| | 1000 | 65 |
| | 3000 | 36 |
| | 9000 | 17 |
| 645093 | 333 | 78 |
| | 1000 | 75 |
| | 3000 | 51 |
| | 9000 | 24 |
| 645094 | 333 | 82 |
| | 1000 | 62 |
| | 3000 | 38 |
| | 9000 | 13 |

TABLE 7-continued

Antisense inhibition of COMP in human tendon cells

| ISIS No. | Concentration (nM) | mRNA level (% Control) |
|---|---|---|
| 645100 | 333 | 73 |
| | 1000 | 61 |
| | 3000 | 45 |
| | 9000 | 32 |
| 645104 | 333 | 82 |
| | 1000 | 58 |
| | 3000 | 46 |
| | 9000 | 24 |
| 645109 | 333 | 68 |
| | 1000 | 33 |
| | 3000 | 16 |
| | 9000 | 9 |

TABLE 8

Antisense inhibition of COMP in human tendon cells

| ISIS No. | Concentration (nM) | mRNA level (% Control) |
|---|---|---|
| 644825 | 333 | 85 |
| | 1000 | 74 |
| | 3000 | 34 |
| | 9000 | 34 |
| 644830 | 333 | 54 |
| | 1000 | 41 |
| | 3000 | 20 |
| | 9000 | 10 |
| 644908 | 333 | 96 |
| | 1000 | 37 |
| | 3000 | 27 |
| | 9000 | 5 |
| 644921 | 333 | 74 |
| | 1000 | 50 |
| | 3000 | 38 |
| | 9000 | 30 |
| 644931 | 333 | 95 |
| | 1000 | 79 |
| | 3000 | 34 |
| | 9000 | 12 |
| 644934 | 333 | 86 |
| | 1000 | 61 |
| | 3000 | 30 |
| | 9000 | 11 |
| 644935 | 333 | 102 |
| | 1000 | 46 |
| | 3000 | 22 |
| | 9000 | 6 |
| 644936 | 333 | 69 |
| | 1000 | 42 |
| | 3000 | 19 |
| | 9000 | 6 |
| 644939 | 333 | 80 |
| | 1000 | 65 |
| | 3000 | 38 |
| | 9000 | 22 |
| 644940 | 333 | 108 |
| | 1000 | 76 |
| | 3000 | 63 |
| | 9000 | 37 |
| 644944 | 333 | 95 |
| | 1000 | 56 |
| | 3000 | 27 |
| | 9000 | 7 |
| 644952 | 333 | 108 |
| | 1000 | 81 |
| | 3000 | 44 |
| | 9000 | 22 |
| 644959 | 333 | 34 |
| | 1000 | 23 |
| | 3000 | 10 |
| | 9000 | 6 |
| 644985 | 333 | 69 |
| | 1000 | 78 |

TABLE 8-continued

Antisense inhibition of COMP in human tendon cells

| ISIS No. | Concentration (nM) | mRNA level (% Control) |
|---|---|---|
| | 3000 | 48 |
| | 9000 | 28 |
| 644998 | 333 | 92 |
| | 1000 | 51 |
| | 3000 | 26 |
| | 9000 | 14 |
| 645002 | 333 | 53 |
| | 1000 | 44 |
| | 3000 | 20 |
| | 9000 | 6 |
| 645005 | 333 | 64 |
| | 1000 | 39 |
| | 3000 | 24 |
| | 9000 | 8 |
| 645015 | 333 | 41 |
| | 1000 | 36 |
| | 3000 | 32 |
| | 9000 | 26 |
| 645026 | 333 | 60 |
| | 1000 | 46 |
| | 3000 | 34 |
| | 9000 | 15 |

TABLE 9

Antisense inhibition of COMP in human tendon cells

| ISIS No. | Concentration (nM) | mRNA level (% Control) |
|---|---|---|
| 644822 | 333 | 86 |
| | 1000 | 77 |
| | 3000 | 65 |
| | 9000 | 59 |
| 644829 | 333 | 86 |
| | 1000 | 56 |
| | 3000 | 44 |
| | 9000 | 13 |
| 644837 | 333 | 112 |
| | 1000 | 81 |
| | 3000 | 63 |
| | 9000 | 29 |
| 644840 | 333 | 67 |
| | 1000 | 63 |
| | 3000 | 47 |
| | 9000 | 46 |
| 644841 | 333 | 46 |
| | 1000 | 46 |
| | 3000 | 25 |
| | 9000 | 25 |
| 644850 | 333 | 44 |
| | 1000 | 27 |
| | 3000 | 8 |
| | 9000 | 2 |
| 644854 | 333 | 59 |
| | 1000 | 27 |
| | 3000 | 27 |
| | 9000 | 4 |
| 644855 | 333 | 64 |
| | 1000 | 51 |
| | 3000 | 19 |
| | 9000 | 17 |
| 644856 | 333 | 47 |
| | 1000 | 50 |
| | 3000 | 25 |
| | 9000 | 15 |
| 644858 | 333 | 51 |
| | 1000 | 25 |
| | 3000 | 8 |
| | 9000 | 1 |
| 644862 | 333 | 113 |
| | 1000 | 92 |
| | 3000 | 47 |
| | 9000 | 24 |

TABLE 9-continued

Antisense inhibition of COMP in human tendon cells

| ISIS No. | Concentration (nM) | mRNA level (% Control) |
|---|---|---|
| 644866 | 333 | 67 |
| | 1000 | 48 |
| | 3000 | 22 |
| | 9000 | 5 |
| 644867 | 333 | 85 |
| | 1000 | 40 |
| | 3000 | 53 |
| | 9000 | 9 |
| 644869 | 333 | 92 |
| | 1000 | 105 |
| | 3000 | 58 |
| | 9000 | 44 |
| 644870 | 333 | 83 |
| | 1000 | 63 |
| | 3000 | 49 |
| | 9000 | 30 |
| 644873 | 333 | 70 |
| | 1000 | 58 |
| | 3000 | 19 |
| | 9000 | 15 |
| 644880 | 333 | 62 |
| | 1000 | 45 |
| | 3000 | 25 |
| | 9000 | 12 |
| 644888 | 333 | 97 |
| | 1000 | 65 |
| | 3000 | 22 |
| | 9000 | 7 |
| 644959 | 333 | 23 |
| | 1000 | 22 |
| | 3000 | 9 |
| | 9000 | 5 |

Example 5: Effect of Antisense Oligonucleotides Targeting Human COMP in Transgenic Mice ISIS 644959 (see Table 2) was selected for evaluation in a bigenic mouse model that expresses mutant human COMP containing the D469 deletion and a FLAG tag (see Posey et al., *Am. J. Pathol.*, 2009, 175, 1555-1563), hereinafter referred to as "COMP D469Δ." Two week old mice were subcutaneously injected with 50 mg/kg ISIS 644959 or PBS two times per week for three weeks (a total of 6 doses). Each treatment group consisted of 2 animals. Four days after the final injection, the mice were sacrificed. The knee joints were carefully dissected, and all soft tissue was removed and homogenized in TRIzol (Life Technologies, Carlsbad, Calif.). RNA was isolated from the growth plate using RNAeasy (Qiagen, Germantown, Md.), and levels of COMP mRNA were evaluated using qRT-PCR with human COMP primers: forward: 5'-GCAATGACACCATCCCAGAG-3', SEQ ID NO: 293; and reverse: 5'-CTTGTCATCGTCGTC-CTTGTAGTC-3', SEQ ID NO: 294. The reverse primer has two nucleobases that are complementary to the COMP sequence, and the remaining nucleobases are complementary to the FLAG tag. The average human COMP mRNA level for the ISIS 644959 treatment group was 75% relative to the PBS treated group.

ISIS 644959 (see Table 2) was further evaluated in the COMP D469Δ transgenic mouse model in a similar experiment. Three week old mice were subcutaneously injected with 50 mg/kg ISIS 644959 or PBS two times per week for two weeks (a total of 4 doses). Each treatment group consisted of 3 animals. One day after the final injection, the mice were sacrificed. The average human COMP mRNA level for the ISIS 644959 treatment group was 56% relative to the PBS treated group.

These results show that antisense oligonucleotides targeting COMP dosed subcutaneously reduced target mRNA levels in the growth plate.

Example 6: Distribution of Antisense Oligonucleotides to Cartilage and Effects on COMP Expression and Cellular Pathology ISIS 644959 (see Table 2) and ISIS 645046 (see Table 3) were evaluated in COMP D469Δ mice. One week old mice were intramuscularly injected with 60 mg/kg of ISIS 644959, ISIS 645046, or PBS vehicle alone three times per week for three weeks (a total of 9 doses). Each treatment group consisted of 3 animals. Once the mice reached 28 days of age (one to two days after the final injection), they were sacrificed and blood, liver, kidney, and hind limb joints were collected. The hind limbs were dissected in order to isolate the growth plates and articular cartilage.

Distribution of Antisense Oligonucleotides to the Growth Plate

In order to determine whether the antisense oliognucleotides were distributed to the growth plates, tibial growth plates were fixed in 95% vol/vol ethanol and immunostained with an antibody that recognizes the antisense oligonucleotide DNA backbone. After antibody staining, the sections were quenched with 3% hydrogen peroxide for 10 to 15 minutes, followed by two, five minute rinses in PBST. DAB chromagen was used to visualize the antibody signal. The resulting images showed that ISIS 644959 and ISIS 645046 distributed to the growth plates of the mice treated with either of those oligonucleotides. In contrast, no signal was detected in the growth plates of the PBS treated mice. ISIS 644959 was also detected in the kidneys and articular cartilage, and no signal was detected in those tissues in the PBS treated mice.

COMP mRNA Expression and Intracellular Retention of COMP Protein

The effects of the COMP targeting antisense oligonucleotides on COMP mRNA expression and intracellular retention of COMP protein in chondrocytes was assessed and compared to that of PBS treated mice. The knee joints of the hind limbs were homogenized and RNA was extracted, as described in Example 5. RT-qPCR was carried out using the primers described in Example 5. The human COMP mRNA levels were normalized to mouse HPRTla levels, and the average results for each treatment group are shown in Table 10 below.

Tibial growth plates fixed in 95% vol/vol ethanol were sectioned and treated with Proteinase K for 2 to 10 minutes at room temperature, then washed twice for five minutes in PBST. Cyto-Q background buster (Innovex Biosciences, Richmond, Calif.) was used to block non-specific binding for 20 minutes, followed by two more PBST rinses. The sections were stained with a human COMP antibody (Cat. no. ab11056, Abcam, Cambridge, Mass.) overnight at 4° C. The signal was visualized using DAB. The resulting images showed that human COMP protein was present in the chondrocytes of the PBS treated COMP D469Δ mice, indicative of high levels of intracellular retained COMP protein. The amount of human COMP protein staining was reduced in images obtained from ISIS 644959 treated animals, indicative of reduced intracellular retention of COMP protein in those animals.

Inflammation and Proliferation

In order to assess the effects of Isis No. 644959 on inflammation and proliferation of chondrocytes, sections of tibial growth plates were stained, as described for COMP protein above, with antibodies against YM1 (cat. no. 01404, Stem Cell Technologies, Vancouver, Canada), IL-16 (cat. no. sc-7902, Santa Cruz Biotechnology, Dallas Tex.), or Ki67 (cat. no. SC-7846, Santa Cruz, Biotechnology, Dallas Tex.). The resulting images showed that treatment with Isis No. 644959 significantly reduced the levels of inflammatory markers YM1 and IL-16 in chondrocytes, relative to PBS treated COMP D469Δ mice. The levels of Ki67 were significantly increased in Isis No. 644959 treated COMP D469Δ mice relative to PBS treated COMP D469Δ mice, indicative of increased chondrocyte proliferation in the antisense oligonucleotide treated mice.

Chondrocyte Death

Hind limbs used to assess chondrocyte death were fixed in 10% wt/vol formalin, and sections were stained via terminal deoxynucleotidyl transferase-mediated deoxyuridine triphosphate-biotin nick end labeling (TUNEL). In PBS treated COMP D469Δ mice, TUNEL positive chondrocytes were observed throughout all zones of the growth plate. In Isis No. 644959 treated COMP D469Δ mice, TUNEL positive condrocytes were primarily restricted to the hypertrophic zone. The percentage of TUNEL positive growth plate chondrocytes was also assessed by counting the cells, and the results are shown in Table 11 below. The decreased TUNEL staining in antisense oligonucleotide treated COMP D469Δ mice indicates that the treatment reduced chondrocyte cell death relative to the PBS treated animals. Altogether, the results from these in vivo experiments indicates that treatment with modified, antisense oligonucleotides dampened the growth plate chondrocyte phenotypes observed in COMP D469Δ mice and restored chondrocyte homeostasis in the growth plate.

TABLE 10

Human COMP mRNA expression

| Treatment (Isis No. or PBS) | mRNA level (% PBS) |
|---|---|
| PBS | 100 |
| 644959 | 62 |
| 645046 | 77 |

TABLE 11

TUNEL positive growth plate chondrocytes

| Treatment (Isis No. or PBS) | TUNEL positive chondrocytes (%) |
|---|---|
| PBS | 90 |
| 644959 | 19 |

What is claimed:

1. A compound comprising a modified oligonucleotide 16 to 30 linked nucleosides in length, wherein the modified oligonucleotide has a nucleobase sequence comprising a portion of at least 16 contiguous nucleobases complementary to an equal length portion of nucleobases 2316-2331, 2319-2334, or 2322-2337 of SEQ ID NO: 1, wherein said modified oligonucleotide is complementary to the linked nucleosides of SEQ ID NO:1.

2. The compound of claim 1, wherein the modified oligonucleotide comprises at least one modified internucleoside linkage, at least one modified sugar, or at least one modified nucleobase.

3. The compound of claim 2, wherein the modified internucleoside linkage is a phosphorothioate internucleoside linkage.

4. The compound of claim 2, wherein the modified sugar is a bicyclic sugar.

5. The compound of claim 4, wherein the bicyclic sugar is selected from the group consisting of: 4'-$(CH_2)$—O-2' (LNA); 4'-$(CH_2)_2$-O-2' (ENA); and 4'-$CH(CH_3)$—O-2' (cEt).

6. The compound of claim 2, wherein the modified sugar is 2'-O-methoxyethyl.

7. The compound of claim 2, wherein the modified nucleobase is a 5-methylcytosine.

8. The compound of claim 1, wherein the modified oligonucleotide comprises:

(a) a gap segment consisting of linked deoxynucleosides;

(b) a 5' wing segment consisting of linked nucleosides; and (c) a 3' wing segment consisting of linked nucleosides;

wherein the gap segment is positioned immediately adjacent to and between the 5' wing segment and the 3' wing segment and wherein each nucleoside of each wing segment comprises a modified sugar.

9. A composition comprising the compound of claim 1 or salt thereof and a pharmaceutically acceptable carrier.

10. A method of inhibiting expression of cartilage oligomeric matrix protein in a cell, comprising administering to the cell a compound of claim 1, thereby reducing expression of cartilage oligomeric matrix protein in a cell.

11. The method of claim 10, wherein the cell is selected from a group consisting of a growth plate cell, a tendon cell, and a cartilage cell.

12. The method of claim 10, wherein the cell is in an animal.

13. The method of claim 12, wherein the animal is a human.

14. A method of treating or ameliorating a disease associated with retention of cartilage oligomeric matrix protein in the enlarged rough endoplasmic reticulum in a subject comprising administering to the subject a compound of claim 1, thereby treating or ameliorating the disease.

15. The method of claim 14, wherein the disease is pseudoachondroplasia.

16. The method of claim 14, wherein the disease is multiple epiphyseal dysplasia.

* * * * *

SEQUENCE LISTING

<160> NUMBER OF SEQ ID NOS: 294

<210> SEQ ID NO 1

<211> LENGTH: 2471
<212> TYPE: DNA
<213> ORGANISM: Homo sapiens

<400> SEQUENCE: 1
agaaagcgag cagccaccca gctccccgcc accgccatgg tccccgacac cgcctgcgtt 60
cttctgctca ccctggctgc cctcggcgcg tccggacagg gccagagccc gttgggctca 120
gacctgggcc cgcagatgct tcgggaactg caggaaacca acgcggcgct gcaggacgtg 180
cgggagctgc tgcggcagca ggtcagggag atcacgttcc tgaaaaacac ggtgatggag 240
tgtgacgcgt gcgggatgca gcagtcagta cgcaccggcc tacccagcgt gcggcccctg 300
ctccactgcg cgcccggctt ctgcttcccc ggcgtggcct gcatccagac ggagagcggc 360
gcgcgctgcg gcccctgccc cgcgggcttc acgggcaacg gctcgcactg caccgacgtc 420
aacgagtgca acgcccaccc ctgcttcccc cgagtccgct gtatcaacac cagcccgggg 480
ttccgctgcg aggcttgccc gccggggtac agcggcccca cccaccaggg cgtggggctg 540
gctttcgcca aggccaacaa gcaggtttgc acggacatca acgagtgtga gaccgggcaa 600
cataactgcg tccccaactc cgtgtgcatc aacacccggg gctccttcca gtgcggcccg 660
tgccagcccg gcttcgtggg cgaccaggcg tccggctgcc agcggcgcgc acagcgcttc 720
tgccccgacg gctcgcccag cgagtgccac gagcatgcag actgcgtcct agagcgcgat 780
ggctcgcggt cgtgcgtgtg tgccgttggc tgggccggca acgggatcct ctgtggtcgc 840
gacactgacc tagacggctt cccggacgag aagctgcgct gcccggagcg ccagtgccgt 900
aaggacaact gcgtgactgt gcccaactca gggcaggagg atgtggaccg cgatggcatc 960
ggagacgcct gcgatccgga tgccgacggg gacggggtcc ccaatgaaaa ggacaactgc 1020
ccgctggtgc ggaacccaga ccagcgcaac acggacgagg acaagtgggg cgatgcgtgc 1080
gacaactgcc ggtcccagaa gaacgacgac caaaaggaca cagaccagga cggccggggc 1140
gatgcgtgcg acgacgacat cgacggcgac cggatccgca accaggccga caactgccct 1200
agggtaccca actcagacca gaaggacagt gatggcgatg gtatagggga tgcctgtgac 1260
aactgtcccc agaagagcaa cccggatcag gcggatgtgg accacgactt tgtgggagat 1320
gcttgtgaca gcgatcaaga ccaggatgga gacggacatc aggactctcg ggacaactgt 1380
cccacggtgc ctaacagtgc ccaggaggac tcagaccacg atggccaggg tgatgcctgc 1440
gacgacgacg acgacaatga cggagtccct gacagtcggg acaactgccg cctggtgcct 1500
aaccccggcc aggaggacgc ggacagggac ggcgtgggcg acgtgtgcca ggacgacttt 1560
gatgcagaca aggtggtaga caagatcgac gtgtgtccgg agaacgctga agtcacgctc 1620
accgacttca gggccttcca gacagtcgtg ctggacccgg agggtgacgc gcagattgac 1680
cccaactggg tggtgctcaa ccagggaagg gagatcgtgc agacaatgaa cagcgaccca 1740
ggcctggctg tgggttacac tgccttcaat ggcgtggact tcgagggcac gttccatgtg 1800
aacacggtca cggatgacga ctatgcgggc ttcatctttg gctaccagga cagctccagc 1860
ttctacgtgg tcatgtggaa gcagatggag caaacgtatt ggcaggcgaa ccccttccgt 1920
gctgtggccg agcctggcat ccaactcaag gctgtgaagt cttccacagg ccccggggaa 1980
cagctgcgga acgctctgtg gcatacagga gacacagagt cccaggtgcg gctgctgtgg 2040
aaggacccgc gaaacgtggg ttggaaggac aagaagtcct atcgttggtt cctgcagcac 2100
cggccccaag tgggctacat cagggtgcga ttctatgagg gccctgagct ggtggccgac 2160
agcaacgtgg tcttggacac aaccatgcgg ggtggccgcc tgggggtctt ctgcttctcc 2220
caggagaaca tcatctgggc caacctgcgt taccgctgca atgacaccat cccagaggac 2280
tatgagaccc atcagctgcg gcaagcctag ggaccagggt gaggacccgc cggatgacag 2340
ccaccctcac cgcggctgga tgggggctct gcacccagcc ccaaggggtg gccgtcctga 2400
gggggaagtg agaagggctc agagaggaca aaataaagtg tgtgtgcagg gaaaaaaaaa 2460
aaaaaaaaaa a 2471

<210> SEQ ID NO 2
<211> LENGTH: 19
<212> TYPE: DNA
<213> ORGANISM: Artificial sequence
<220> FEATURE:
<223> OTHER INFORMATION: Primer

<400> SEQUENCE: 2
cgcagatgct tcgggaact 19

<210> SEQ ID NO 3
<211> LENGTH: 22
<212> TYPE: DNA
<213> ORGANISM: Artificial sequence
<220> FEATURE:
<223> OTHER INFORMATION: Primer

<400> SEQUENCE: 3
cactccatca ccgtgttttt ca 22

<210> SEQ ID NO 4
<211> LENGTH: 19
<212> TYPE: DNA
<213> ORGANISM: Artificial sequence
<220> FEATURE:
<223> OTHER INFORMATION: Probe

<400> SEQUENCE: 4
aaaccaacgc ggcgctgca 19

<210> SEQ ID NO 5
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 5
cgcaggcggt gtcggg 16

<210> SEQ ID NO 6
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 6
gcagaagaac gcaggc 16

<210> SEQ ID NO 7
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 7
gcgccgaggg cagcca 16

<210> SEQ ID NO 8
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 8
ccctgtccgg acgcgc 16

<210> SEQ ID NO 9
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 9
aacgggctct ggccct 16

<210> SEQ ID NO 10
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 10
aggtctgagc ccaacg 16

<210> SEQ ID NO 11
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 11
tgactgctgc atcccg 16

<210> SEQ ID NO 12
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 12
cgctgggtag gccggt 16

<210> SEQ ID NO 13
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 13
gggcgcgcag tggagc 16

<210> SEQ ID NO 14
<211> LENGTH: 16

```
<212> TYPE: DNA
<213> ORGANISM: Artificial sequence
<220> FEATURE:
<223> OTHER INFORMATION: Synthetic oligonucleotide

<400> SEQUENCE: 14

gaagcagaag ccgggc                                                    16


<210> SEQ ID NO 15
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 15

gtctggatgc aggcca                                                    16


<210> SEQ ID NO 16
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 16

ccgctctccg tctgga                                                    16


<210> SEQ ID NO 17
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 17

ccgcagcgcg cgccgc                                                    16


<210> SEQ ID NO 18
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 18

agccgttgcc cgtgaa                                                    16


<210> SEQ ID NO 19
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 19

gtcggtgcag tgcgag                                                    16


<210> SEQ ID NO 20
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 20
```

ggcaagcctc gcagcg 16

<210> SEQ ID NO 21
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 21
ccgctgtacc ccggcg 16

<210> SEQ ID NO 22
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 22
ccacgccctg gtgggt 16

<210> SEQ ID NO 23
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 23
ttggcgaaag ccagcc 16

<210> SEQ ID NO 24
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 24
gttgatgtcc gtgcaa 16

<210> SEQ ID NO 25
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 25
gttatgttgc ccggtc 16

<210> SEQ ID NO 26
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 26
tgatgcacac ggagtt 16

<210> SEQ ID NO 27
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 27
tggaaggagc cccggg 16

<210> SEQ ID NO 28
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 28
ggctggcacg ggccgc 16

<210> SEQ ID NO 29
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 29
tggtcgccca cgaagc 16

<210> SEQ ID NO 30
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 30
cgcgccgctg gcagcc 16

<210> SEQ ID NO 31
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 31
tcgctgggcg agccgt 16

<210> SEQ ID NO 32
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 32
tctaggacgc agtctg 16

<210> SEQ ID NO 33
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 33
gagccatcgc gctcta 16

<210> SEQ ID NO 34
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 34
acgcacgacc gcgagc 16

<210> SEQ ID NO 35
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 35
gaggatcccg ttgccg 16

<210> SEQ ID NO 36
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 36
tgtcgcgacc acagag 16

<210> SEQ ID NO 37
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 37
gaagccgtct aggtca 16

<210> SEQ ID NO 38
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 38
gcgctccggg cagcgc 16

<210> SEQ ID NO 39
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 39
gtcacgcagt tgtcct 16

<210> SEQ ID NO 40
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 40
gagttgggca cagtca 16

<210> SEQ ID NO 41
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 41
cccgtcggca tccgga 16

<210> SEQ ID NO 42
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 42
gtctgggttc cgcacc 16

<210> SEQ ID NO 43
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 43
gccccacttg tcctcg 16

<210> SEQ ID NO 44
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 44
gggaccggca gttgtc 16

<210> SEQ ID NO 45
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 45
tcgtcgttct tctggg 16

<210> SEQ ID NO 46
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 46
ccccggccgt cctggt 16

<210> SEQ ID NO 47

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 47
ggatccggtc gccgtc 16

<210> SEQ ID NO 48
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 48
cggcctggtt gcggat 16

<210> SEQ ID NO 49
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 49
ctgagttggg taccct 16

<210> SEQ ID NO 50
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 50
cgggttgctc ttctgg 16

<210> SEQ ID NO 51
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 51
catccgcctg atccgg 16

<210> SEQ ID NO 52
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 52
gctgtcacaa gcatct 16

<210> SEQ ID NO 53
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 53
ggtcttgatc gctgtc 16

<210> SEQ ID NO 54
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 54
ctccatcctg gtcttg 16

<210> SEQ ID NO 55
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 55
gtcccgagag tcctga 16

<210> SEQ ID NO 56
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 56
gggcactgtt aggcac 16

<210> SEQ ID NO 57
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 57
ctcctgggca ctgtta 16

<210> SEQ ID NO 58
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 58
gactgtcagg gactcc 16

<210> SEQ ID NO 59
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 59
gttaggcacc aggcgg 16

<210> SEQ ID NO 60
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 60
cgcccacgcc gtccct 16

<210> SEQ ID NO 61
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 61
ttgtctacca ccttgt 16

<210> SEQ ID NO 62
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 62
cacgatctcc cttccc 16

<210> SEQ ID NO 63
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 63
cgtttgctcc atctgc 16

<210> SEQ ID NO 64
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 64
aggctcggcc acagca 16

<210> SEQ ID NO 65
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 65
gagttggatg ccaggc 16

<210> SEQ ID NO 66
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 66
ctctgtgtct cctgta 16

-continued

<210> SEQ ID NO 67
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 67
gccgcacctg ggactc 16

<210> SEQ ID NO 68
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 68
ccaacgatag gacttc 16

<210> SEQ ID NO 69
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 69
ctgtcggcca ccagct 16

<210> SEQ ID NO 70
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 70
cccaggcggc cacccc 16

<210> SEQ ID NO 71
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 71
cgcaggttgg cccaga 16

<210> SEQ ID NO 72
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 72
ttgcagcggt aacgca 16

<210> SEQ ID NO 73
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 73
atgggtctca tagtcc 16

<210> SEQ ID NO 74
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 74
ttgccgcagc tgatgg 16

<210> SEQ ID NO 75
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 75
ggtccctagg cttgcc 16

<210> SEQ ID NO 76
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 76
ggcgggtcct caccct 16

<210> SEQ ID NO 77
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 77
gtccttctgg tctgag 16

<210> SEQ ID NO 78
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 78
acgcaggcgg tgtcgg 16

<210> SEQ ID NO 79
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 79
tgagcagaag aacgca 16

<210> SEQ ID NO 80
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 80
gacgcgccga gggcag 16

<210> SEQ ID NO 81
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 81
tggccctgtc cggacg 16

<210> SEQ ID NO 82
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 82
cccaacgggc tctggc 16

<210> SEQ ID NO 83
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 83
tactgactgc tgcatc 16

<210> SEQ ID NO 84
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 84
gcacgctggg taggcc 16

<210> SEQ ID NO 85
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 85
gccgggcgcg cagtgg 16

<210> SEQ ID NO 86
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 86
gggaagcaga agccgg 16

<210> SEQ ID NO 87
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 87
tccgtctgga tgcagg 16

<210> SEQ ID NO 88
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 88
gcgccgctct ccgtct 16

<210> SEQ ID NO 89
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 89
gggccgcagc gcgcgc 16

<210> SEQ ID NO 90
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 90
gcgagccgtt gcccgt 16

<210> SEQ ID NO 91
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 91
cgtcggtgca gtgcga 16

<210> SEQ ID NO 92
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 92
cggcgggcaa gcctcg 16

<210> SEQ ID NO 93
<211> LENGTH: 16

-continued

<212> TYPE: DNA
<213> ORGANISM: Artificial sequence
<220> FEATURE:
<223> OTHER INFORMATION: Synthetic oligonucleotide

<400> SEQUENCE: 93
gggccgctgt accccg 16

<210> SEQ ID NO 94
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 94
gccccacgcc ctggtg 16

<210> SEQ ID NO 95
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 95
gccttggcga aagcca 16

<210> SEQ ID NO 96
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 96
cccggtctca cactcg 16

<210> SEQ ID NO 97
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 97
gcagttatgt tgcccg 16

<210> SEQ ID NO 98
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 98
ccccgggtgt tgatgc 16

<210> SEQ ID NO 99
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 99
cactggaagg agcccc 16

<210> SEQ ID NO 100
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 100
acgaagccgg gctggc 16

<210> SEQ ID NO 101
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 101
gcctggtcgc ccacga 16

<210> SEQ ID NO 102
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 102
gtgcgcgccg ctggca 16

<210> SEQ ID NO 103
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 103
gcactcgctg ggcgag 16

<210> SEQ ID NO 104
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 104
cgctctagga cgcagt 16

<210> SEQ ID NO 105
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 105
cgcgagccat cgcgct 16

<210> SEQ ID NO 106
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 106
acacacgcac gaccgc 16

<210> SEQ ID NO 107
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 107
acagaggatc ccgttg 16

<210> SEQ ID NO 108
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 108
cagtgtcgcg accaca 16

<210> SEQ ID NO 109
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 109
gcagcgcagc ttctcg 16

<210> SEQ ID NO 110
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 110
cttacggcac tggcgc 16

<210> SEQ ID NO 111
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 111
acagtcacgc agttgt 16

<210> SEQ ID NO 112
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 112
atccggatcg caggcg 16

<210> SEQ ID NO 113
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 113
ccccgtcccc gtcggc 16

<210> SEQ ID NO 114
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 114
ttgcgctggt ctgggt 16

<210> SEQ ID NO 115
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 115
atcgccccac ttgtcc 16

<210> SEQ ID NO 116
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 116
tgggaccggc agttgt 16

<210> SEQ ID NO 117
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 117
ttggtcgtcg ttcttc 16

<210> SEQ ID NO 118
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 118
cgccccggcc gtcctg 16

<210> SEQ ID NO 119
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 119
tgcggatccg gtcgcc 16

<210> SEQ ID NO 120
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 120
cagttgtcgg cctggt 16

<210> SEQ ID NO 121
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 121
taccatcgcc atcact 16

<210> SEQ ID NO 122
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 122
atccgggttg ctcttc 16

<210> SEQ ID NO 123
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 123
cacatccgcc tgatcc 16

<210> SEQ ID NO 124
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 124
cgctgtcaca agcatc 16

<210> SEQ ID NO 125
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 125
tggtcttgat cgctgt 16

<210> SEQ ID NO 126

-continued

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 126
tctccatcct ggtctt 16

<210> SEQ ID NO 127
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 127
agttgtcccg agagtc 16

<210> SEQ ID NO 128
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 128
ctgggcactg ttaggc 16

<210> SEQ ID NO 129
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 129
agtcctcctg ggcact 16

<210> SEQ ID NO 130
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 130
cccgactgtc agggac 16

<210> SEQ ID NO 131
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 131
cgtcctcctg gccggg 16

<210> SEQ ID NO 132
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 132
accttgtctg catcaa 16

<210> SEQ ID NO 133
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 133
atcttgtcta ccacct 16

<210> SEQ ID NO 134
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 134
ctgcacgatc tccctt 16

<210> SEQ ID NO 135
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 135
ttcgcctgcc aatacg 16

<210> SEQ ID NO 136
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 136
gccaggctcg gccaca 16

<210> SEQ ID NO 137
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 137
tgtggaagac ttcaca 16

<210> SEQ ID NO 138
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 138
gggactctgt gtctcc 16

<210> SEQ ID NO 139
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 139
tcgcgggtcc ttccac 16

<210> SEQ ID NO 140
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 140
ggccctcata gaatcg 16

<210> SEQ ID NO 141
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 141
ttgctgtcgg ccacca 16

<210> SEQ ID NO 142
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 142
acccccaggc ggccac 16

<210> SEQ ID NO 143
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 143
taacgcaggt tggccc 16

<210> SEQ ID NO 144
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 144
attgcagcgg taacgc 16

<210> SEQ ID NO 145
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 145
gctgatgggt ctcata 16

<210> SEQ ID NO 146
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 146
gcttgccgca gctgat 16

<210> SEQ ID NO 147
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 147
caccctggtc cctagg 16

<210> SEQ ID NO 148
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 148
tccggcgggt cctcac 16

<210> SEQ ID NO 149
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 149
gaacgcaggc ggtgtc 16

<210> SEQ ID NO 150
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 150
gggtgagcag aagaac 16

<210> SEQ ID NO 151
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 151
ccggacgcgc cgaggg 16

<210> SEQ ID NO 152
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 152
ctctggccct gtccgg 16

<210> SEQ ID NO 153
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 153
gagcccaacg ggctct 16

<210> SEQ ID NO 154
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 154
ctgcatcccg cacgcg 16

<210> SEQ ID NO 155
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 155
cgtactgact gctgca 16

<210> SEQ ID NO 156
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 156
gccgcacgct gggtag 16

<210> SEQ ID NO 157
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 157
gaagccgggc gcgcag 16

<210> SEQ ID NO 158
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 158
atgcaggcca cgccgg 16

<210> SEQ ID NO 159
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 159
ctctccgtct ggatgc 16

<210> SEQ ID NO 160
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 160
cgcgcgccgc tctccg 16

<210> SEQ ID NO 161
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 161
ccgtgaagcc cgcggg 16

<210> SEQ ID NO 162
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 162
gcagtgcgag ccgttg 16

<210> SEQ ID NO 163
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 163
atacagcgga ctcggg 16

<210> SEQ ID NO 164
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 164
accccggcgg gcaagc 16

<210> SEQ ID NO 165
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 165
ggtggggccg ctgtac 16

<210> SEQ ID NO 166
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 166
aagccagccc cacgcc 16

<210> SEQ ID NO 167
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 167
ttggccttgg cgaaag 16

<210> SEQ ID NO 168
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 168
ttgcccggtc tcacac 16

<210> SEQ ID NO 169
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 169
gacgcagtta tgttgc 16

<210> SEQ ID NO 170
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 170
gagccccggg tgttga 16

<210> SEQ ID NO 171
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 171
ccgcactgga aggagc 16

<210> SEQ ID NO 172
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 172
cccacgaagc cgggct 16

<210> SEQ ID NO 173
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 173
gctggcagcc ggacgc 16

<210> SEQ ID NO 174
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 174
gctgtgcgcg ccgctg 16

<210> SEQ ID NO 175
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 175
gtggcactcg ctgggc 16

<210> SEQ ID NO 176
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 176
tcgcgctcta ggacgc 16

<210> SEQ ID NO 177
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 177
gaccgcgagc catcgc 16

<210> SEQ ID NO 178
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 178
ggcacacacg cacgac 16

<210> SEQ ID NO 179
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 179
gaccacagag gatccc 16

<210> SEQ ID NO 180
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 180
aggtcagtgt cgcgac 16

<210> SEQ ID NO 181
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 181
cgggcagcgc agcttc 16

<210> SEQ ID NO 182
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 182
gtccttacgg cactgg 16

<210> SEQ ID NO 183
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 183
ggcacagtca cgcagt 16

<210> SEQ ID NO 184
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 184
ggcatccgga tcgcag 16

<210> SEQ ID NO 185
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 185
ccgcaccagc gggcag 16

<210> SEQ ID NO 186
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 186
gtgttgcgct ggtctg 16

<210> SEQ ID NO 187
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 187
cgcatcgccc cacttg 16

<210> SEQ ID NO 188
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 188
ttctgggacc ggcagt 16

<210> SEQ ID NO 189
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 189
tgtgtccttt tggtcg 16

<210> SEQ ID NO 190
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 190
tcgcacgcat cgcccc 16

<210> SEQ ID NO 191
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 191
ggttgcggat ccggtc 16

<210> SEQ ID NO 192
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 192
agggcagttg tcggcc 16

<210> SEQ ID NO 193
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 193
cctataccat cgccat 16

<210> SEQ ID NO 194
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 194
cctgatccgg gttgct 16

<210> SEQ ID NO 195
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 195
agcatctccc acaaag 16

<210> SEQ ID NO 196
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 196
tcgctgtcac aagcat 16

<210> SEQ ID NO 197
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 197
cctggtcttg atcgct 16

<210> SEQ ID NO 198
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 198
agagtcctga tgtccg 16

<210> SEQ ID NO 199
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 199
gttaggcacc gtggga 16

<210> SEQ ID NO 200
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 200
cctgggcact gttagg 16

<210> SEQ ID NO 201
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 201
tgtcagggac tccgtc 16

<210> SEQ ID NO 202
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 202
tgtcccgact gtcagg 16

<210> SEQ ID NO 203
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 203
cgccgtccct gtccgc 16

<210> SEQ ID NO 204
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 204
accaccttgt ctgcat 16

<210> SEQ ID NO 205

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 205
tcgatcttgt ctacca 16

<210> SEQ ID NO 206
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 206
agtgtaaccc acagcc 16

<210> SEQ ID NO 207
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 207
gggttcgcct gccaat 16

<210> SEQ ID NO 208
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 208
gatgccaggc tcggcc 16

<210> SEQ ID NO 209
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 209
gcctgtggaa gacttc 16

<210> SEQ ID NO 210
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 210
cctgggactc tgtgtc 16

<210> SEQ ID NO 211
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 211
gtttcgcggg tccttc 16

<210> SEQ ID NO 212
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 212
cagggccctc atagaa 16

<210> SEQ ID NO 213
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 213
tgtgtccaag accacg 16

<210> SEQ ID NO 214
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 214
gaagaccccc aggcgg 16

<210> SEQ ID NO 215
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 215
cggtaacgca ggttgg 16

<210> SEQ ID NO 216
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 216
catagtcctc tgggat 16

<210> SEQ ID NO 217
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 217
gcagctgatg ggtctc 16

<210> SEQ ID NO 218
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 218
taggcttgcc gcagct 16

<210> SEQ ID NO 219
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 219
ctcaccctgg tcccta 16

<210> SEQ ID NO 220
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 220
tcatccggcg ggtcct 16

<210> SEQ ID NO 221
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 221
gaagaacgca ggcggt 16

<210> SEQ ID NO 222
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 222
gccagggtga gcagaa 16

<210> SEQ ID NO 223
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 223
tgtccggacg cgccga 16

<210> SEQ ID NO 224
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 224
gggctctggc cctgtc 16

<210> SEQ ID NO 225
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 225
tctgagccca acgggc 16

<210> SEQ ID NO 226
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 226
ctgctgcatc ccgcac 16

<210> SEQ ID NO 227
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 227
tgggtaggcc ggtgcg 16

<210> SEQ ID NO 228
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 228
cgcgcagtgg agcagg 16

<210> SEQ ID NO 229
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 229
gcagaagccg ggcgcg 16

<210> SEQ ID NO 230
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 230
tggatgcagg ccacgc 16

<210> SEQ ID NO 231
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 231
gctctccgtc tggatg 16

<210> SEQ ID NO 232
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 232
cagcgcgcgc cgctct 16

<210> SEQ ID NO 233
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 233
tgcccgtgaa gcccgc 16

<210> SEQ ID NO 234
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 234
ggtgcagtgc gagccg 16

<210> SEQ ID NO 235
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 235
tgatacagcg gactcg 16

<210> SEQ ID NO 236
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 236
ctgtaccccg gcgggc 16

<210> SEQ ID NO 237
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 237
ctggtgggtg gggccg 16

<210> SEQ ID NO 238
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 238
gcgaaagcca gcccca 16

<210> SEQ ID NO 239
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 239
gatgtccgtg caaacc 16

<210> SEQ ID NO 240
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 240
atgttgcccg gtctca 16

<210> SEQ ID NO 241
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 241
tgcacacgga gttggg 16

<210> SEQ ID NO 242
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 242
aaggagcccc gggtgt 16

<210> SEQ ID NO 243
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 243
tggcacgggc cgcact 16

<210> SEQ ID NO 244
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 244
tcgcccacga agccgg 16

<210> SEQ ID NO 245
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 245
gccgctggca gccgga 16

<210> SEQ ID NO 246
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 246
ctgggcgagc cgtcgg 16

<210> SEQ ID NO 247
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 247
cgcagtctgc atgctc 16

<210> SEQ ID NO 248
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 248
ccatcgcgct ctagga 16

<210> SEQ ID NO 249
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 249
cacgaccgcg agccat 16

<210> SEQ ID NO 250
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 250
gatcccgttg ccggcc 16

<210> SEQ ID NO 251
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 251
cgcgaccaca gaggat 16

<210> SEQ ID NO 252
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 252
tctaggtcag tgtcgc 16

<210> SEQ ID NO 253
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 253
ctccgggcag cgcagc 16

<210> SEQ ID NO 254
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 254
gttgtcctta cggcac 16

<210> SEQ ID NO 255
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 255
ttgggcacag tcacgc 16

<210> SEQ ID NO 256
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 256
gtcggcatcc ggatcg 16

<210> SEQ ID NO 257
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 257
gttccgcacc agcggg 16

<210> SEQ ID NO 258
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 258
cgtccgtgtt gcgctg 16

<210> SEQ ID NO 259
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 259
gcacgcatcg ccccac 16

<210> SEQ ID NO 260
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 260
ttcttctggg accggc 16

<210> SEQ ID NO 261
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 261
tctgtgtcct tttggt 16

<210> SEQ ID NO 262
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 262
tccggtcgcc gtcgat 16

<210> SEQ ID NO 263
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 263
cctggttgcg gatccg 16

<210> SEQ ID NO 264
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 264
cctagggcag ttgtcg 16

<210> SEQ ID NO 265
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 265
cccctatacc atcgcc 16

<210> SEQ ID NO 266
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 266
ccgcctgatc cgggtt 16

<210> SEQ ID NO 267
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 267
tcacaagcat ctccca 16

<210> SEQ ID NO 268
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 268
cttgatcgct gtcaca 16

<210> SEQ ID NO 269
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 269
catcctggtc ttgatc 16

<210> SEQ ID NO 270
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 270
ccgagagtcc tgatgt 16

<210> SEQ ID NO 271
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 271
actgttaggc accgtg 16

<210> SEQ ID NO 272
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 272
tcctgggcac tgttag 16

<210> SEQ ID NO 273
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 273
ctgtcaggga ctccgt 16

<210> SEQ ID NO 274
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 274
cggcagttgt cccgac 16

<210> SEQ ID NO 275
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 275
ccacgccgtc cctgtc 16

<210> SEQ ID NO 276
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 276
tctaccacct tgtctg 16

<210> SEQ ID NO 277
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 277
ctccgggtcc agcacg 16

<210> SEQ ID NO 278
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 278
ggcagtgtaa cccaca 16

<210> SEQ ID NO 279
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 279
ctcggccaca gcacgg 16

<210> SEQ ID NO 280
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 280
ttggatgcca ggctcg 16

<210> SEQ ID NO 281
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 281
ccgcagctgt tccccg 16

<210> SEQ ID NO 282
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 282
gcacctggga ctctgt 16

<210> SEQ ID NO 283
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 283
acgataggac ttcttg 16

<210> SEQ ID NO 284

<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 284
ggccaccagc tcaggg 16

<210> SEQ ID NO 285
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 285
ggttgtgtcc aagacc 16

<210> SEQ ID NO 286
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 286
gcagaagacc cccagg 16

<210> SEQ ID NO 287
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 287
cagcggtaac gcaggt 16

<210> SEQ ID NO 288
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 288
ggtctcatag tcctct 16

<210> SEQ ID NO 289
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 289
gccgcagctg atgggt 16

<210> SEQ ID NO 290
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 290

-continued

```
ccctaggctt gccgca                                                    16


<210> SEQ ID NO 291
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 291

gggtcctcac cctggt                                                    16


<210> SEQ ID NO 292
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 292

ctgtcatccg gcgggt                                                    16


<210> SEQ ID NO 293
<211> LENGTH: 20
<212> TYPE: DNA
<213> ORGANISM: Artificial Sequence
<220> FEATURE:
<223> OTHER INFORMATION: Primer

<400> SEQUENCE: 293

gcaatgacac catcccagag                                                20


<210> SEQ ID NO 294
<211> LENGTH: 24
<212> TYPE: DNA
<213> ORGANISM: Artificial sequence
<220> FEATURE:
<223> OTHER INFORMATION: Primer

<400> SEQUENCE: 294

cttgtcatcg tcgtccttgt agtc                                           24
```